(12) United States Patent
Kang et al.

(10) Patent No.: US 10,259,996 B2
(45) Date of Patent: Apr. 16, 2019

(54) BOROLE COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventors: Sunwoo Kang, Yongin-si (KR); Sangho Jeon, Yongin-si (KR); Youngmi Cho, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/584,826

(22) Filed: May 2, 2017

(65) Prior Publication Data

US 2018/0057737 A1 Mar. 1, 2018

(30) Foreign Application Priority Data

Aug. 23, 2016 (KR) ........................ 10-2016-0106989

(51) Int. Cl.
| | |
|---|---|
| *C09K 11/63* | (2006.01) |
| *C07F 5/02* | (2006.01) |
| *C07D 333/10* | (2006.01) |
| *C07D 251/14* | (2006.01) |
| *C07D 317/10* | (2006.01) |
| *C07D 333/32* | (2006.01) |
| *C07D 333/50* | (2006.01) |

(Continued)

(52) U.S. Cl.
CPC ............ *C09K 11/63* (2013.01); *C07D 251/14* (2013.01); *C07D 317/10* (2013.01); *C07D 333/10* (2013.01); *C07D 333/32* (2013.01); *C07D 333/50* (2013.01); *C07F 5/02* (2013.01); *C09K 11/06* (2013.01); *C09K 11/56* (2013.01); *C09K 11/632* (2013.01); *C07C 2603/72* (2017.05)

(58) Field of Classification Search
None
See application file for complete search history.

(56) References Cited

U.S. PATENT DOCUMENTS

| | | |
|---|---|---|
| 8,513,702 B2 | 8/2013 | Schmid et al. |
| 2015/0115239 A1 | 4/2015 | Pflumm et al. |
| 2017/0040536 A1 | 2/2017 | Kang et al. |

FOREIGN PATENT DOCUMENTS

| | | |
|---|---|---|
| KR | 10-2010-0050455 | 5/2010 |
| KR | 10-2014-0146103 | 12/2014 |
| KR | 10-2017-0018236 | 2/2017 |

OTHER PUBLICATIONS

Huynh, Keith, et al. "Perfluoropentaphenylborole: A New Approach to Lewis Acidic, Electron-Deficient Compounds", Angew. Chem. Int. Ed., 2009, vol. 48, pp. 2835-2837.

(Continued)

*Primary Examiner* — Jay Yang
(74) *Attorney, Agent, or Firm* — Lewis Roca Rothgerber Christie LLP

(57) ABSTRACT

A borole compound is represented by Formula 1: $X_{11}$—$(R_{11})_{b11}$. $X_{11}$, $R_{11}$, and b11 are as defined herein. An organic light-emitting device includes the borole compound. The organic light-emitting device includes a first electrode, a second electrode, and an organic layer between the first electrode and the second electrode, the organic layer including an emission layer. The organic layer includes the borole compound.

20 Claims, 4 Drawing Sheets

(51) Int. Cl.
*C09K 11/06* (2006.01)
*C09K 11/56* (2006.01)

(56) References Cited

OTHER PUBLICATIONS

Méndez, Henry, et al., "Doping of Organic Semiconductors: Impact of Dopant Strength and Electronic Coupling" Angew. Chem., 2013, vol. 125, pp. 7905-7909.

| 190 |
|---|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

BOROLE COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2016-0106989, filed on Aug. 23, 2016, in the Korean Intellectual Property Office, the entire content of which is incorporated herein by reference.

BACKGROUND

1. Field

One or more embodiments relate to a borole compound and an organic light-emitting device including the same.

2. Description of the Related Art

Organic light-emitting devices are self-emission devices that produce full-color images, and also have wide viewing angles, high contrast ratios, short response times, as well as excellent characteristics in terms of brightness, driving voltage, and response speed.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state, thereby generating light.

SUMMARY

One or more embodiments include a borole compound and an organic light-emitting device including the same.

Additional aspects of embodiments will be set forth in part in the description which follows and, in part, will be apparent from the description, or may be learned by practice of the presented embodiments.

According to one or more embodiments, a borole compound is represented by Formula 1:

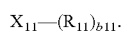    Formula 1

In Formula 1, $X_{11}$ may be selected from a substituted or unsubstituted triazine, a substituted or unsubstituted vinylene carbonate, a substituted or unsubstituted thiophene, a substituted or unsubstituted furan, a substituted or unsubstituted dibenzoborole, a substituted or unsubstituted azulene, a substituted or unsubstituted naphthalene, a substituted or unsubstituted anthracene, and a substituted or unsubstituted pyrene, and $R_{11}$ may be represented by one of Formulae 2-1 to 2-3:

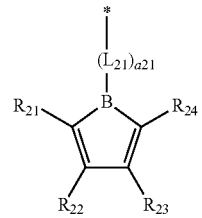
2-1

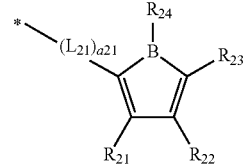
2-2

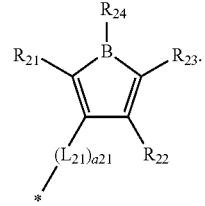
2-3

In Formula 1, b11 may be selected from 1, 2, 3, 4, 5, 6, 7, 8, 9, and 10, wherein, when b11 is two or more, a plurality of $R_{11}$(s) may be identical to or different from each other.

In Formulae 2-1 to 2-3, $L_{21}$ may be selected from a substituted or unsubstituted $C_1$-$C_{10}$ alkylene group, a substituted or unsubstituted $C_2$-$C_{10}$ alkenylene group, a $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a21 may be 0 or 1, $R_{21}$ to $R_{24}$ may each independently be selected from $R_{EW}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), provided that at least one of $R_{21}$ to $R_{24}$ is $R_{EW}$, $R_{EW}$ indicates an electron withdrawing group, and

* indicates a binding site to a neighboring atom.

According to one or more embodiments, an organic light-emitting device includes: a first electrode; a second electrode; an organic layer between the first electrode and the second electrode, the organic layer including an emission layer, wherein the organic layer includes the borole compound described above.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic view of an organic light-emitting device according to an embodiment;

FIGS. 5-7 are schematic views of organic light-emitting devices according to embodiments.

DETAILED DESCRIPTION

Figure 2:
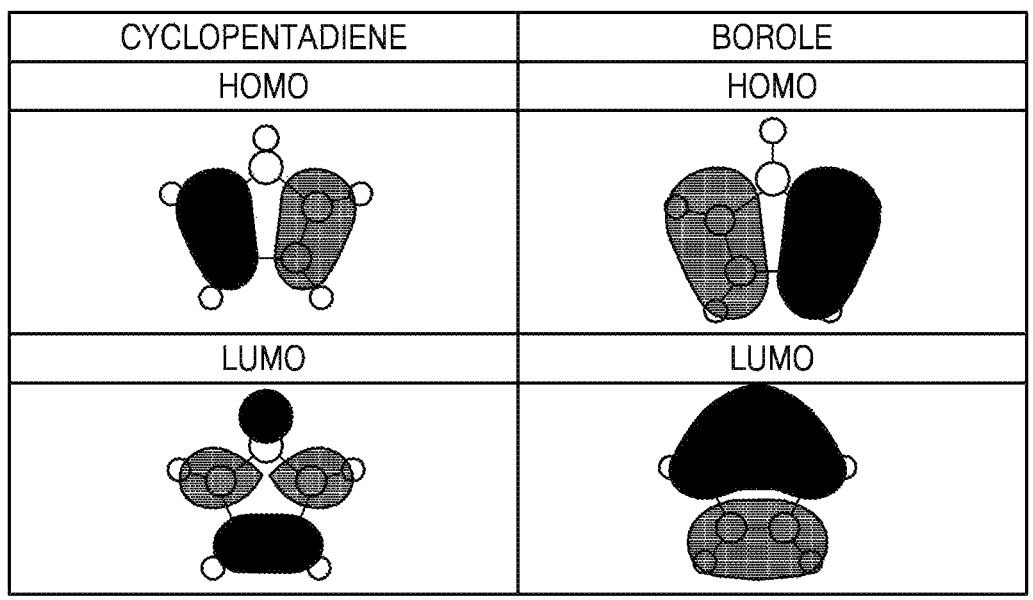
FIG. 2 is a view showing highest occupied molecular orbital (HOMO) and lowest unoccupied molecular orbital (LUMO) distributions of cyclopentadiene and borole.

A borole compound according to an embodiment may be represented by Formula 1:

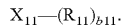   Formula 1

$X_{11}$ in Formula 1 may be selected from a substituted or unsubstituted triazine, a substituted or unsubstituted vinylene carbonate, a substituted or unsubstituted thiophene, a substituted or unsubstituted furan, a substituted or unsubstituted dibenzoborole, a substituted or unsubstituted azulene, a substituted or unsubstituted naphthalene, a substituted or unsubstituted anthracene, and a substituted or unsubstituted pyrene.

For example, $X_{11}$ in Formula 1 may be represented by one of Formulae 3-1 to 3-9, but embodiments of the present disclosure are not limited thereto:

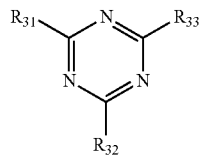   3-1

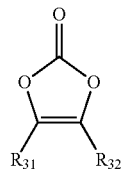   3-2

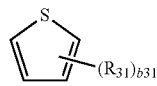   3-3

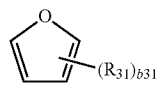   3-4

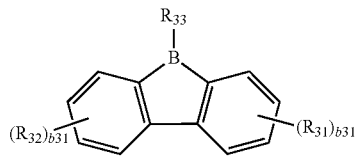   3-5

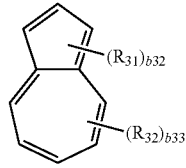   3-6

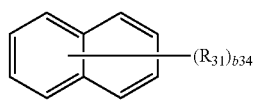   3-7

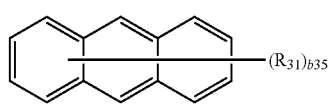   3-8

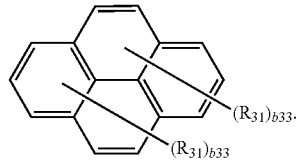   3-9

In Formulae 3-1 to 3-9, $R_{31}$ to $R_{33}$ may each independently be selected from:

a binding site to $R_{11}$, hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group, at least one selected from $R_{31}$, the number of which is the same as b11, may be a binding site to $R_{11}$, at least one selected from $R_{31}$ and $R_{32}$, the number of which is the same as b11, may be a binding site to $R_{11}$, or at least one selected from $R_{31}$ to $R_{33}$, the number of which is the same as b11, may be a binding site to $R_{11}$, b31 may be selected from 1, 2, 3, and 4,
b32 may be selected from 1, 2, and 3,
b33 may be selected from 1, 2, 3, 4, and 5,
b34 may be selected from 1, 2, 3, 4, 5, and 6, and
b35 may be selected from 1, 2, 3, 4, 5, 6, 7, 8, 9, and 10.

In one or more embodiments, $R_{31}$ to $R_{33}$ in Formulae 3-1 to 3-9 may each independently be selected from:

hydrogen, deuterium, —F, —Cl, —Br, —I, a hydroxyl group, a cyano group, a nitro group, a $C_1$-$C_{10}$ alkyl group, and a $C_1$-$C_{10}$ alkoxy group;

a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group; and a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, but embodiments of the present disclosure are not limited thereto.

In one or more embodiments, $R_{31}$ to $R_{33}$ in Formulae 3-1 to 3-9 may each independently be selected from:

hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group, but embodiments of the present disclosure are not limited thereto.

In one or more embodiments, $X_{11}$ in Formula 1 may be represented by one of Formulae 4-1 to 4-9, but embodiments of the present disclosure are not limited thereto:

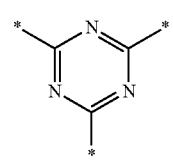

4-1

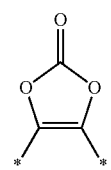

4-2

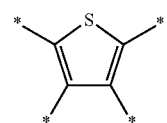

4-3

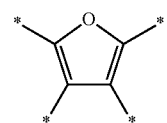

4-4

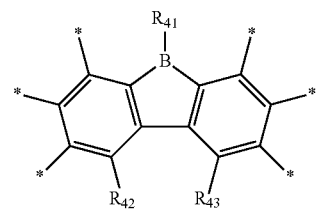

4-5

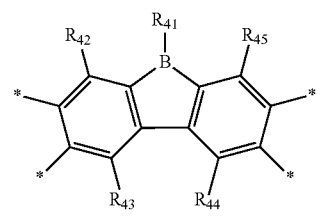

4-6

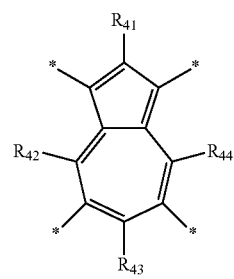

4-7

4-8

4-9

In Formulae 4-1 to 4-9,

* indicates a binding site to $R_{11}$, and $R_{41}$ to $R_{46}$ may each independently be selected from:

hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

$R_{11}$ in Formula 1 may be represented by one of Formulae 2-1 to 2-3:

2-1

2-2

2-3

In Formulae 2-1 to 2-3,

* indicates a binding site to $X_{11}$, and $L_{21}$, a21, and $R_{21}$ to $R_{24}$ are the same as described below.

$L_{21}$ in Formulae 2-1 to 2-3a may be selected from a substituted or unsubstituted $C_1$-$C_{10}$ alkylene group, a substituted or unsubstituted $C_2$-$C_{10}$ alkenylene group, a $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_{21}$ in Formulae 2-1 to 2-3 may be selected from:

a phenylene group, a naphthylene group, a pyridinylene group, a pyrimidinylene group, a pyrazinylene group, and a triazinylene group; and a phenylene group, a naphthylene group, a pyridinylene group, a pyrimidinylene group, a pyrazinylene group, and a triazinylene group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group, but embodiments of the present disclosure are not limited thereto.

In one or more embodiments, $L_{21}$ in Formulae 2-1 to 2-3 may be selected from a phenylene group, a naphthylene group, a pyridinylene group, a pyrimidinylene group, a pyrazinylene group, and a triazinylene group, but embodiments of the present disclosure are not limited thereto.

a21 in Formulae 2-1 to 2-3 indicates the repeating number of $L_{21}$(s) and may be 0 or 1. When a21 is 0, $(L_{21})_{a21}$ may be a single bond.

For example, a21 in Formulae 2-1 to 2-3 may be 0, but embodiments of the present disclosure are not limited thereto.

$R_{21}$ to $R_{24}$ in Formulae 2-1 to 2-3 may each independently be selected from $R_{EW}$ (as used herein, "$R_{EW}$" indicates an electron withdrawing group), hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

For example, $R_{21}$ to $R_{24}$ in Formulae 2-1 to 2-3 may each independently be selected from:

$R_{EW}$, hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group, provided that at least one of $R_{21}$ to $R_{24}$ is $R_{EW}$, but embodiments of the present disclosure are not limited thereto.

In one or more embodiments, $R_{21}$ to $R_{24}$ in Formulae 2-1 to 2-3 may each independently be selected from:

$R_{EW}$, hydrogen, deuterium, —F, —Cl, —Br, —I, a hydroxyl group, a cyano group, a nitro group, a $C_1$-$C_{10}$ alkyl group, and a $C_1$-$C_{10}$ alkoxy group;

a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group; and a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, provided that at least one of $R_{21}$ to $R_{24}$ is $R_{EW}$, but embodiments of the present disclosure are not limited thereto.

In one or more embodiments, $R_{21}$ to $R_{24}$ in Formulae 2-1 to 2-3 may each independently be selected from:

$R_{EW}$, hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group, provided that at least one of $R_{21}$ to $R_{24}$ is $R_{EW}$, but embodiments of the present disclosure are not limited thereto.

For example, $R_{11}$ in Formula 1 may be represented by Formula 2-1, but embodiments of the present disclosure are not limited thereto.

In one or more embodiments, $R_{11}$ in Formula 1 may be represented by one of Formulae 2-11 to 2-19, but embodiments of the present disclosure are not limited thereto:

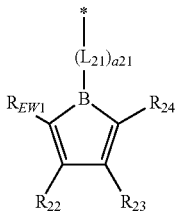

2-11

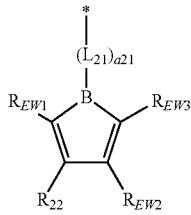

2-12

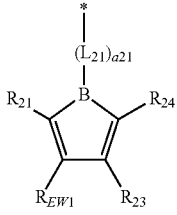

2-13

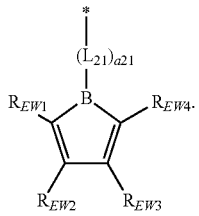

2-14

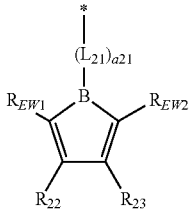

2-15

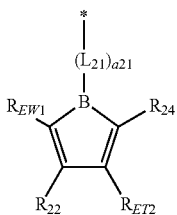

2-16

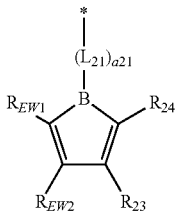

2-17

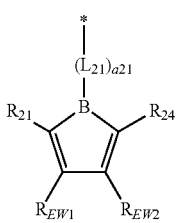

2-18

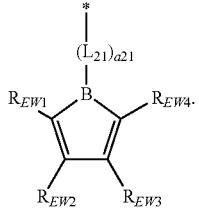

2-19

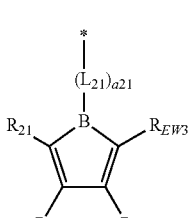

In Formulae 2-11 to 2-19, $L_{21}$ may be selected from a phenylene group, a naphthylene group, a pyridinylene group, a pyrimidinylene group, a pyrazinylene group, and a triazinylene group, a21 may be 0 or 1, $R_{21}$ to $R_{24}$ may each independently be selected from:

$R_{EW}$, hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

$R_{EW1}$ to $R_{EW4}$ may each be an electron withdrawing group, and

* indicates a binding site to $X_{11}$.

In one or more embodiments, $R_{11}$ in Formula 1 may be represented by Formula 2-19, but embodiments of the present disclosure are not limited thereto:

2-19

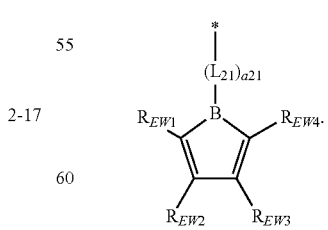

In Formula 2-19, $(L_{21})_{a21}$ may be a single bond, $R_{EW1}$ to $R_{EW4}$ may each independently be selected from —F, —Cl, —Br, —I, a cyano group, a nitro group, —CF$_3$, —CCl$_3$, —CBr$_3$, —Cl$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, and

* indicates a binding site to X$_{11}$.

b11 in Formula 1 indicates the number of R$_{11}$(s) and may be selected from 1, 2, 3, 4, 5, 6, 7, 8, 9, and 10. When b11 is two or more, a plurality of R$_{11}$(s) may be identical to or different from each other.

R$_{EW}$ in Formula 1 indicates an electron withdrawing group.

For example, R$_{EW}$ may be selected from:
—F, —Cl, —Br, —I, a cyano group, and a nitro group; and
a C$_1$-C$_{10}$ alkyl group and a C$_2$-C$_{10}$ alkenyl group, each substituted with at least one selected from —F, —Cl, —Br, —I, a cyano group, and a nitro group, but embodiments of the present disclosure are not limited thereto.

In one or more embodiments, as used throughout the present application, including the claims, R$_{EW}$ may be selected from —F, —Cl, —Br, —I, a cyano group, a nitro group, —CF$_3$, —CCl$_3$, —CBr$_3$, —Cl$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, but embodiments of the present disclosure are not limited thereto.

In one or more embodiments, in Formula 1, X$_{11}$ may be represented by one of Formulae 4-1 to 4-9, and R$_{11}$ may be represented by one of Formulae 2-11 to 2-19, and b11 may be selected from 1, 2, 3, 4, 5, 6, 7, 8, 9, and 10, wherein, when b11 is two or more, a plurality of R$_{11}$(s) may be identical to or different from each other.

In Formulae 4-1 to 4-9,

* indicates a binding site to R$_{11}$, and

R$_{41}$ to R$_{46}$ may each independently be selected from:

hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

In Formulae 2-11 to 2-19, (L$_{21}$)$_{a21}$ may be a single bond,

R$_{21}$ to R$_{24}$ may each independently be selected from:

R$_{EW}$, hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group, R$_{EW1}$ to R$_{EW4}$ may each independently be selected from —F, —Cl, —Br, —I, a cyano group, a nitro group, —CF$_3$, —CCl$_3$, —CBr$_3$, —Cl$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, and

* indicates a binding site to X$_{11}$, but embodiments of the present disclosure are not limited thereto.

In one or more embodiments, in Formula 1, X$_{11}$ may be represented by one of Formulae 4-1 to 4-9, and R$_{11}$ may be represented by Formula 2-19, b11 may be selected from 1, 2, 3, 4, 5, 6, 7, 8, 9, and 10, wherein, when b11 is two or more, a plurality of R$_{11}$(s) may be identical to or different from each other.

In Formulae 4-1 to 4-9,

* indicates a binding site to R$_{11}$, and

R$_{41}$ to R$_{46}$ may each independently be selected from:

hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

In Formula 2-19, (L$_{21}$)$_{a21}$ may be a single bond,

R$_{EW1}$ to R$_{EW4}$ may each independently be selected from —F, —Cl, —Br, —I, a cyano group, a nitro group, —CF$_3$, —CCl$_3$, —CBr$_3$, —Cl$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, and

* indicates a binding site to X$_{11}$, but embodiments of the present disclosure are not limited thereto.

In one or more embodiments, the borole compound represented by Formula 1 may be selected from Compounds 1 to 9, but embodiments of the present disclosure are not limited thereto:

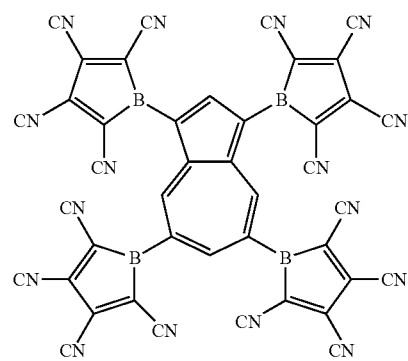

1

2
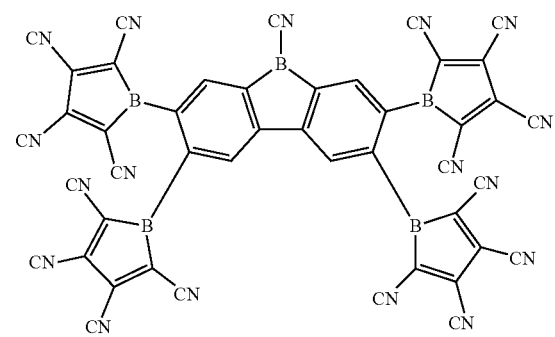
3
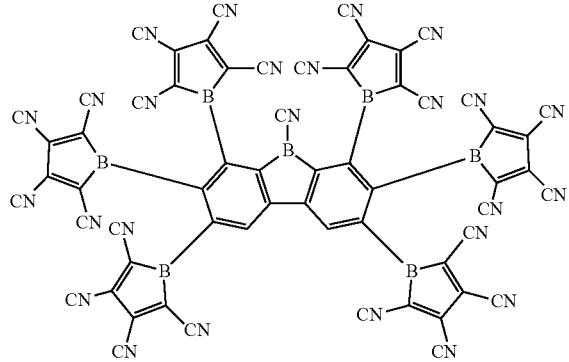
4
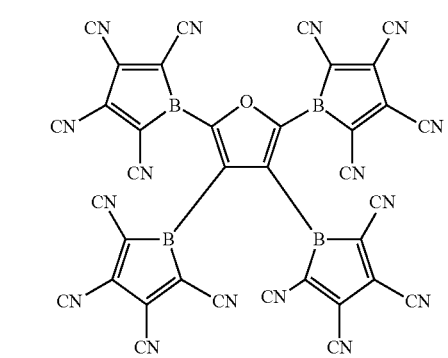
5
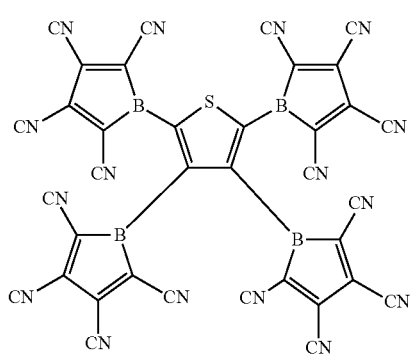
5
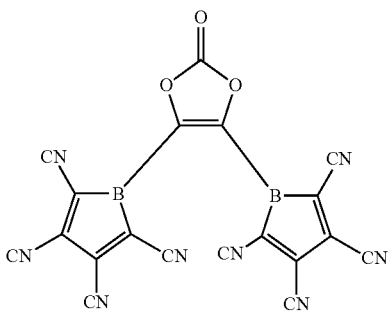
6
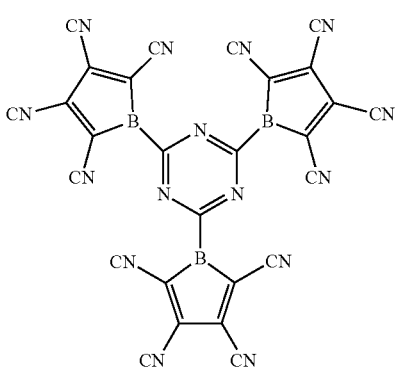
7
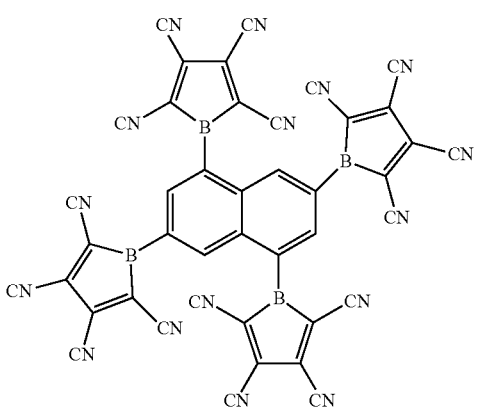
8
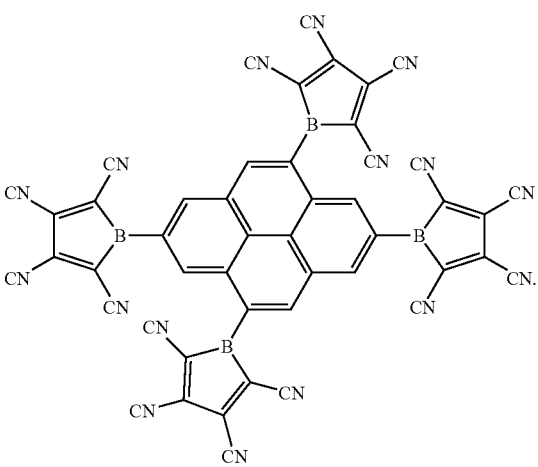
9
The borole compound represented by Formula 1 includes (or essentially includes) a borole structure represented by one of Formulae 2-1 to 2-3.

Referring to FIG. 2, in a borole structure, a molecular orbital contributing to a lowest unoccupied molecular orbital (LUMO) is large, as compared with a boron (B)-free cyclopentadiene structure. This means that borole has stronger electron acceptor characteristics than cyclopentadiene. Accordingly, the borole compound represented by Formula 1, which has the borole structure, may have a relatively high electron affinity (for example, the borole compound may have a higher electron affinity than the compound including cyclopentadiene (or pyrrole) by about 2.35 eV).

Figure 3:
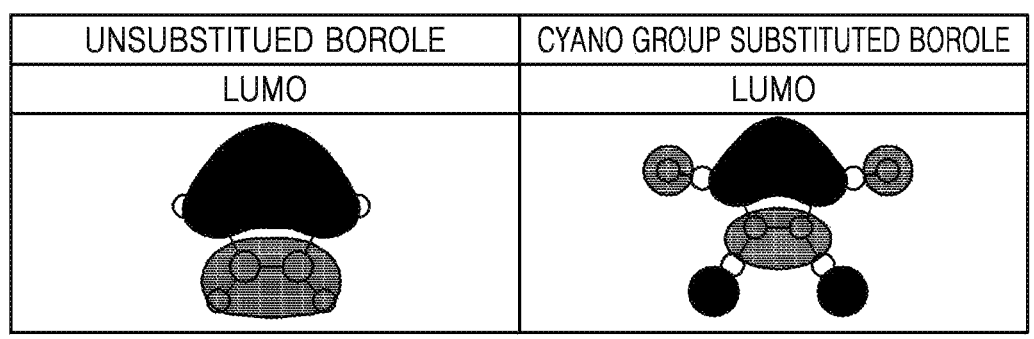
FIG. 3 is a view showing LUMO distributions of unsubstituted borole and borole substituted with a cyano group.

Also, referring to FIG. 3, it can be seen that an electron density of LUMO is further delocalized by introducing the electron withdrawing group, such as a cyano group, into the borole structure. Accordingly, when the electron withdrawing group, such as a cyano group, is introduced into the borole structure, a LUMO energy level of such a compound may be reduced, and the electron affinity of such a component may be increased.

Also, by introducing the electron withdrawing group into the borole structure, a compound having a high electron affinity may be provided.

Therefore, the borole compound represented by Formula 1, according to one or more embodiments, may have a high electron affinity because the borole compound has a structure in which $R_{11}$ having a strong electron withdrawing group is substituted with an $X_{11}$ core having strong electron acceptor characteristics.

An electron affinity of the borole compound represented by Formula 1 may be in a range of about 5.5 eV to about 6.0 eV. When the electron affinity of the borole compound represented by Formula 1 is within this range, a borole compound having a relatively low hole injection barrier may be provided.

A hole injection barrier of the borole compound represented by Formula 1 may be in a range of about 0.1 eV to about 0.4 eV. When the hole injection barrier of the borole compound represented by Formula 1 is within this range, a hole injection barrier at an interface between the anode and the organic layer may be reduced. Accordingly, an organic light-emitting device including the borole compound may have high efficiency and a low driving voltage.

The borole compound represented by Formula 1 may be used between a pair of electrodes of an organic light-emitting device. For example, the borole compound may be included in a hole transport region, for example, a hole injection layer and/or a buffer layer. Therefore, an organic light-emitting device includes a first electrode, a second electrode, and an organic layer between the first electrode and the second electrode, the organic layer including an emission layer, wherein the organic layer includes at least one of the borole compound represented by Formula 1.

For example, the first electrode may be an anode, the second electrode may be a cathode, the organic layer may further include a hole transport region between the first electrode and the emission layer, and the hole transport region may include the borole compound, but embodiments of the present disclosure are not limited thereto.

In one or more embodiments, the hole transport region may include a hole injection layer including the borole compound, or the hole transport region may include a buffer layer including the borole compound, but embodiments of the present disclosure are not limited thereto.

In one or more embodiments, the hole transport region may include a hole injection layer including the borole compound and a buffer layer including the borole compound, but embodiments of the present disclosure are not limited thereto.

In one or more embodiments, the hole injection layer may further include a matrix material, and an amount of the borole compound in the hole injection layer may be in a range of greater than 0 wt % and equal to or smaller than 6 wt % based on a total weight of the hole injection layer, but embodiments of the present disclosure are not limited thereto. For example, the amount of the borole compound in the hole injection layer may be in a range of 1 wt % to 4 wt % based on the total weight of the hole injection layer, but embodiments of the present disclosure are not limited thereto. When the amount of the borole compound is within this range, a hole injection barrier between two neighboring layers may be reduced.

In one or more embodiments, the buffer layer may further include a matrix material, an amount of the borole compound in the buffer layer may be in a range of greater than 0 wt % and equal to or smaller than 6 wt % based on a total weight of the buffer layer, but embodiments of the present disclosure are not limited thereto. For example, the amount of the borole compound in the buffer layer may be in a range of 1 wt % to 4 wt % based on the total weight of the buffer layer, but embodiments of the present disclosure are not limited thereto. When the amount of the borole compound is within this range, a hole injection barrier between two neighboring layers may be reduced.

The matrix material may be selected from the compounds included in the hole transport region to be described below, but embodiments of the present disclosure are not limited thereto.

The expression "(an organic layer) includes at least one borole compound" used herein may include a case in which "(an organic layer) includes one borole compound represented by Formula 1" and a case in which "(an organic layer) includes two or more different borole compounds represented by Formula 1."

For example, the organic layer may include, as the borole compound, only Compound 1. In this regard, Compound 1 may be present in a hole injection layer of the organic light-emitting device. In one or more embodiments, the organic layer may include, as the borole compound, Compound 1 and Compound 2. In one or more embodiments, Compound 1 and Compound 2 may both be present in an identical or same layer (for example, Compound 1 and Compound 2 may both be present in a hole injection layer), or may be present in different layers (for example, Compound 1 may be present in a hole injection layer and Compound 2 may be present in a buffer layer).

The organic layer includes i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. In one or more embodiment, at least one of the hole injection layer and the buffer layer may include the borole compound represented by Formula 1.

The term "organic layer" used herein refers to a single (or sole) layer and/or a plurality of layers disposed between the first electrode and the second electrode of the organic light-emitting device. A material included in the "organic layer" is not limited to an organic material.

[Description of FIG. 1]

Figure 1:
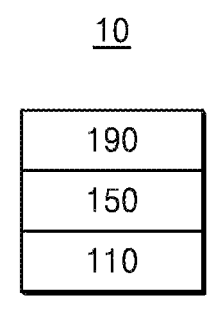

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having, for example, excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflective electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto. As used herein, the terms "combination thereof" and "combinations thereof" may refer to a chemical combination (e.g., an alloy or chemical compound), a mixture, or a laminated structure of components.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single (or sole) layer including a single (or sole) material, ii) a single-layered structure including a single (or sole) layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single (or sole) layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein for each structure, constituting layers are sequentially stacked from the first electrode 110 in this stated order, but the structure of the hole transport region is not limited thereto.

The hole transport region may include at least one selected from m-MTDATA, TDATA, 2-TNATA, NPB (NPD), p-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly (4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

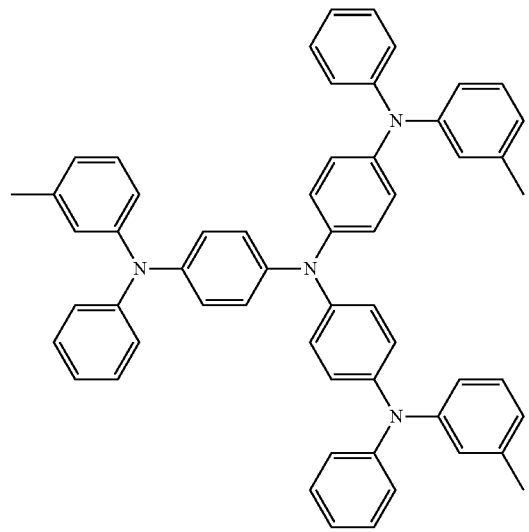

m-MTDATA

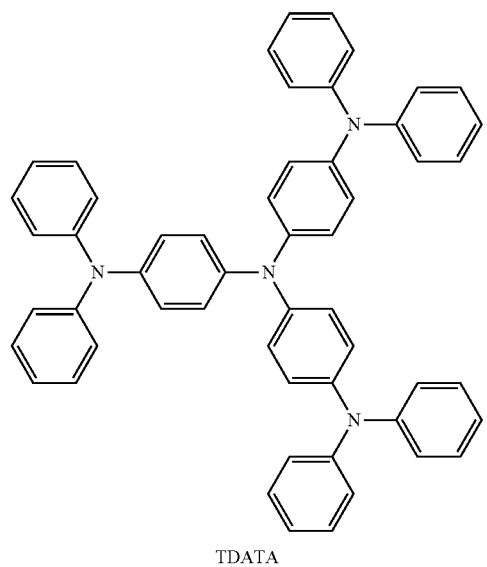

TDATA

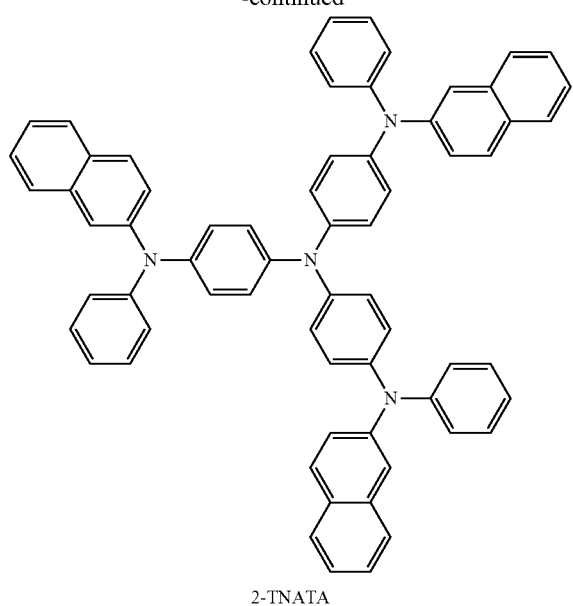
2-TNATA
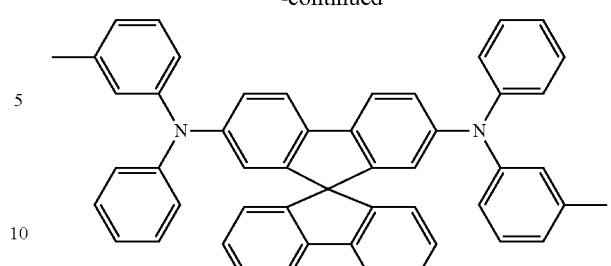
Spiro-TPD
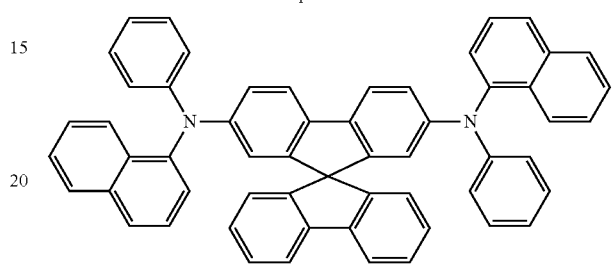
Spiro-NPB
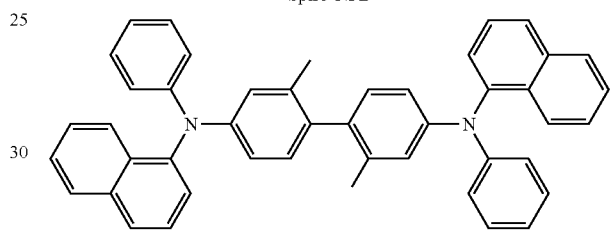
methylated NPB
NPB
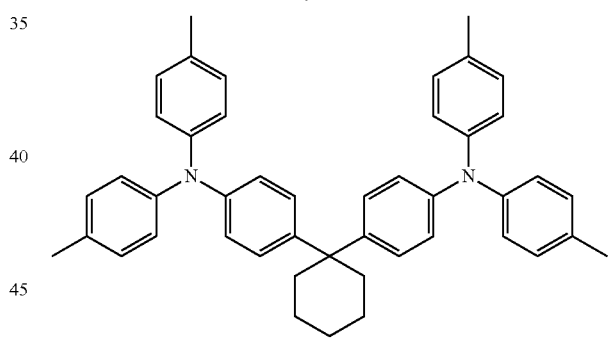
TAPC
β-NPB
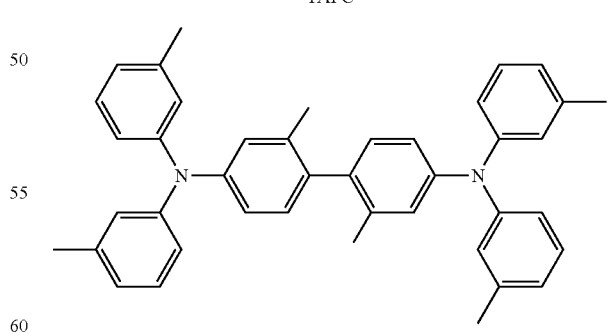
HMTPD
TPD
Formula 201
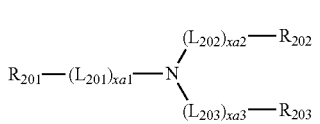

Formula 202

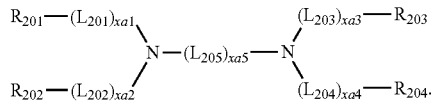

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, and a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$); and $Q_{31}$ to $Q_{33}$ may be the same as described above.

In one or more embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, at least one selected from $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group.

The compound represented by Formula 201 may be represented by Formula 201A:

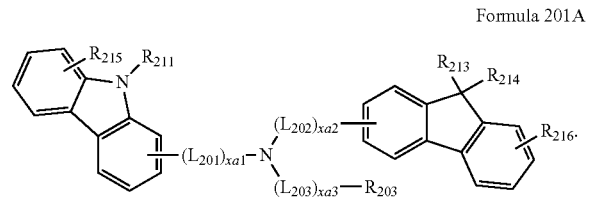

Formula 201A

For example, the compound represented by Formula 201 may be represented by Formula 201A(1), but embodiments of the present disclosure are not limited thereto:

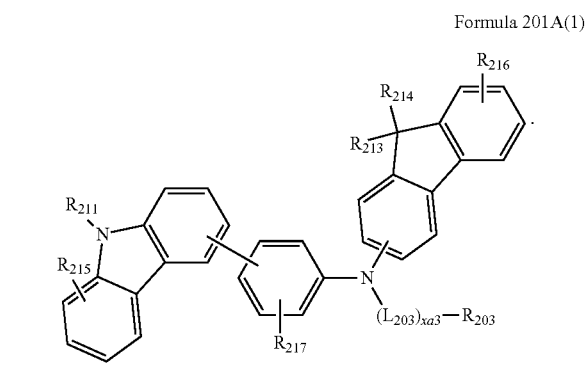

Formula 201A(1)

In one or more embodiments, the compound represented by Formula 201 may be represented by Formula 201A-1, but embodiments of the present disclosure are not limited thereto:

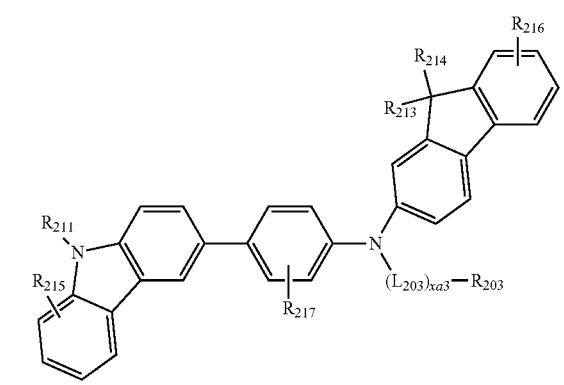

<Formula 201A-1>

The compound represented by Formula 202 may be represented by Formula 202A:

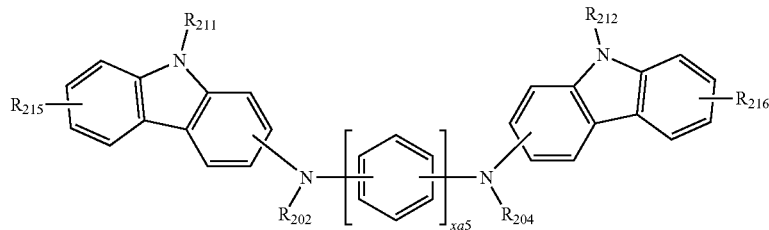

Formula 202A

In one or more embodiments, the compound represented by Formula 202 may be represented by Formula 202A-1:

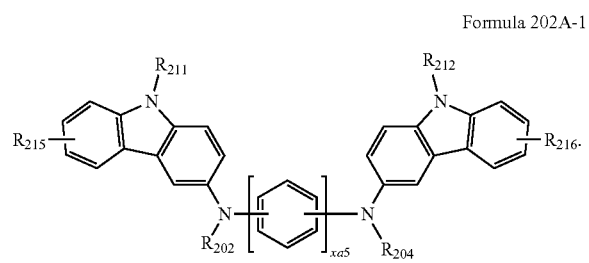

Formula 202A-1

In Formulae 201A, 201A(1), 201A-1, 202A, and 202A-1, $L_{201}$ to $L_{203}$, xa1 to xa3, xa5, and $R_{202}$ to $R_{204}$ may be the same as described above, $R_{211}$ and $R_{212}$ may be the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

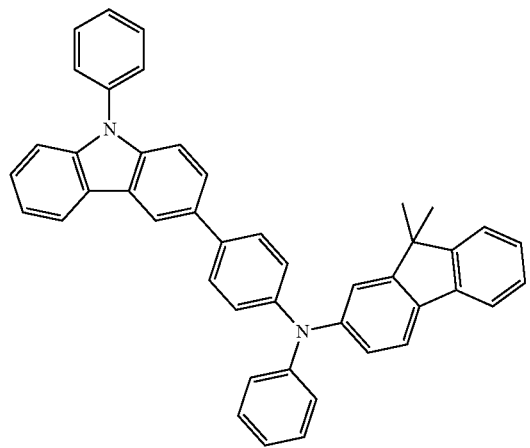

HT1

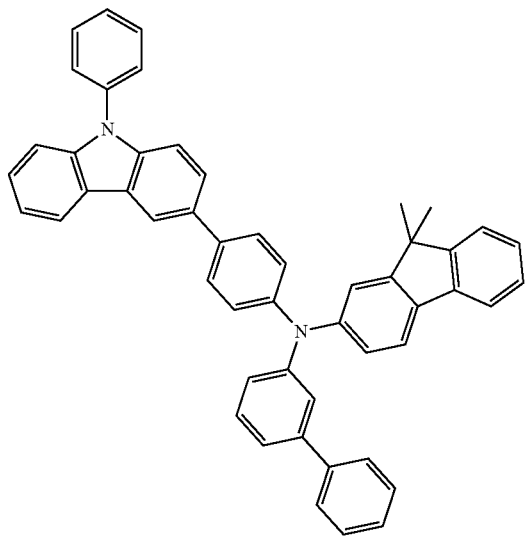

HT2

-continued
HT3
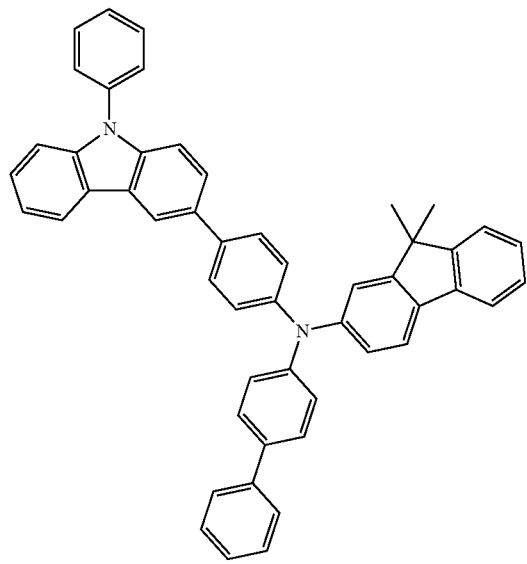
HT4
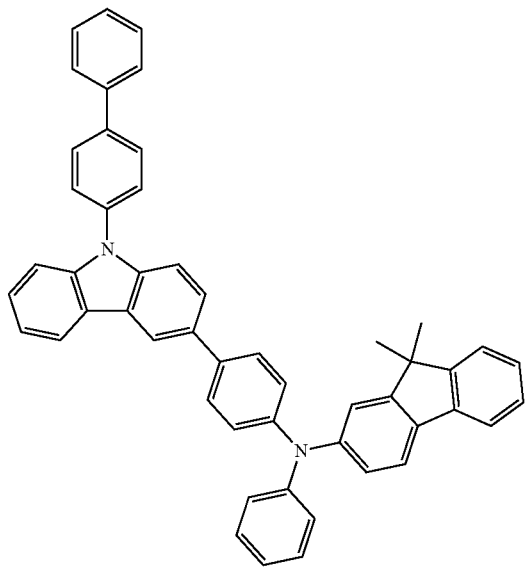
HT5
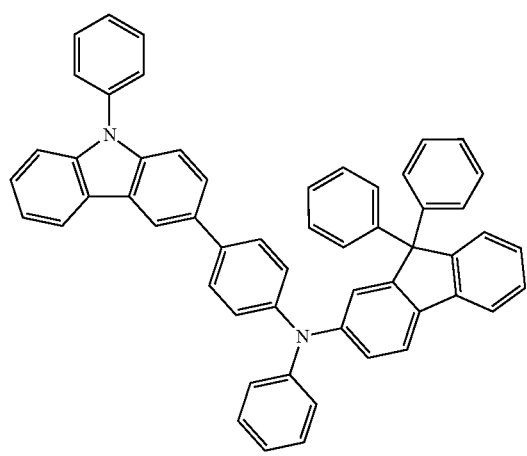
HT6
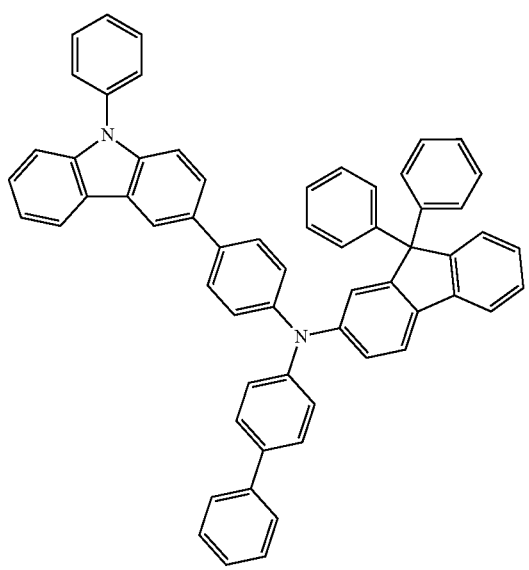

HT7
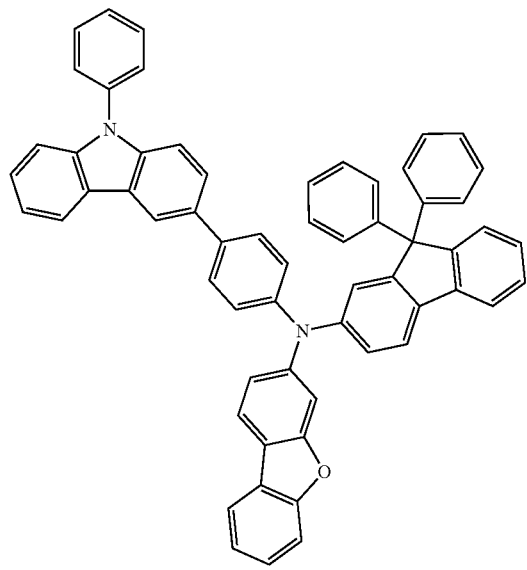
HT8
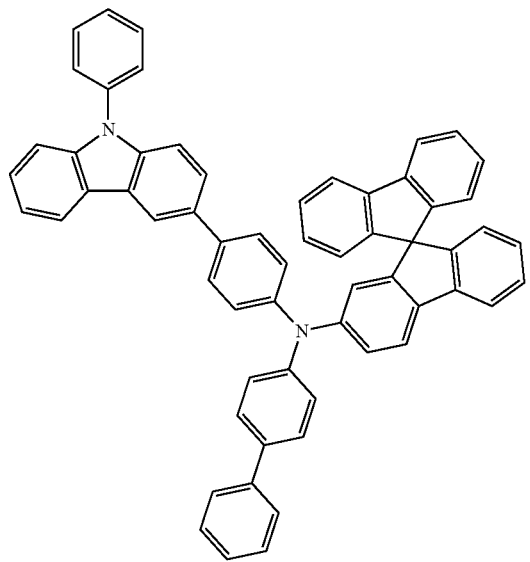
HT9
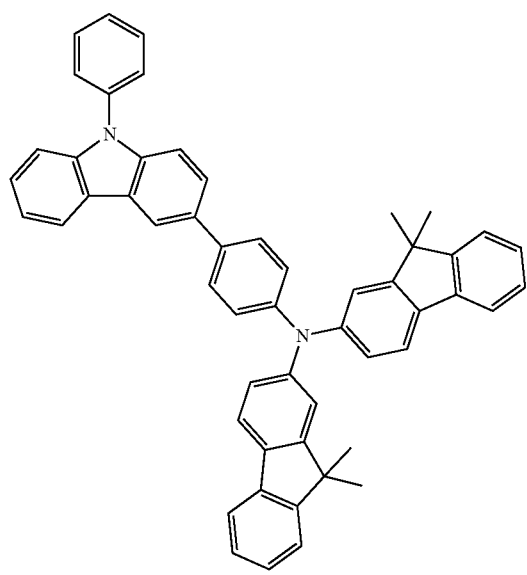
HT10
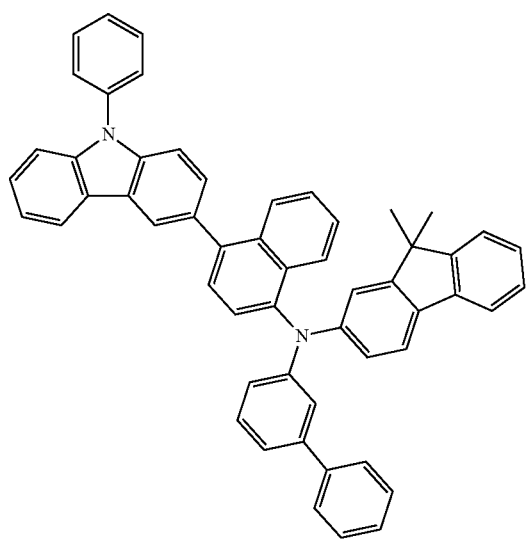

-continued
HT11
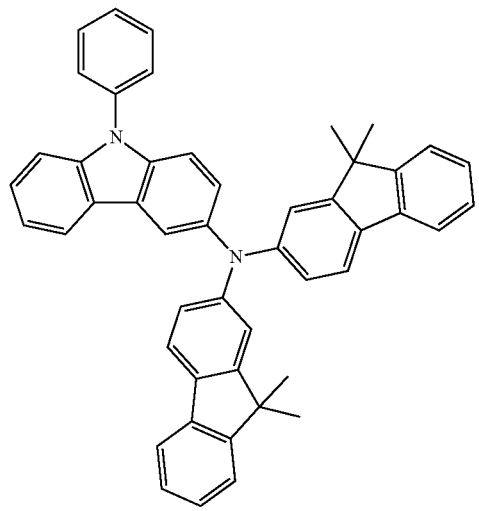
HT12
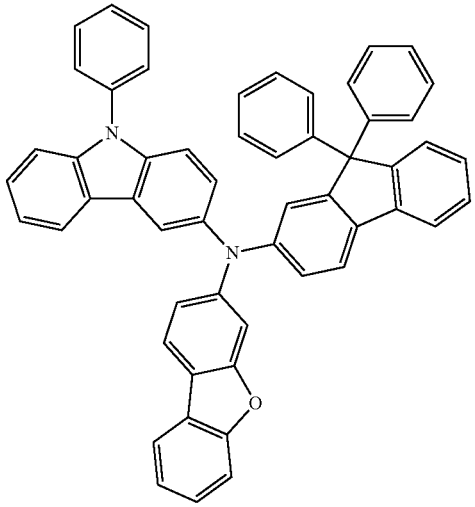
HT13
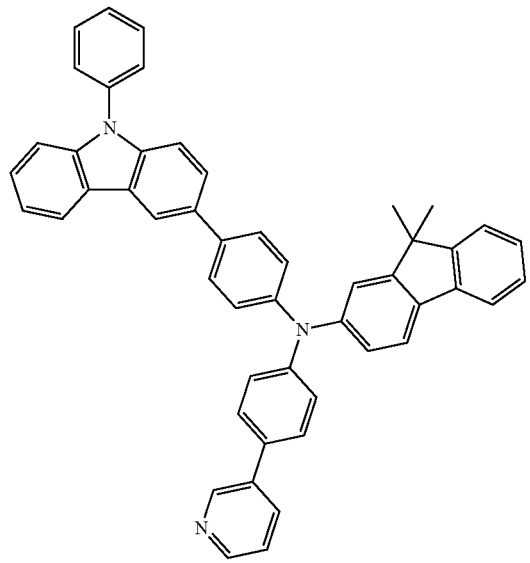
HT14
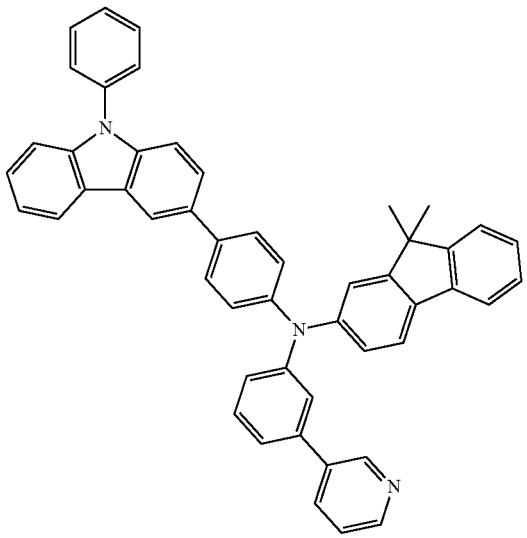
HT15
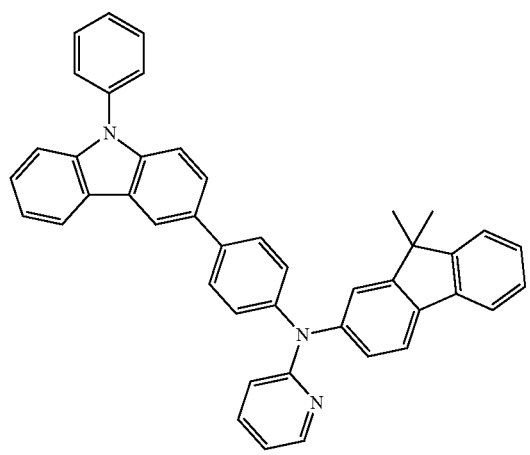
HT16
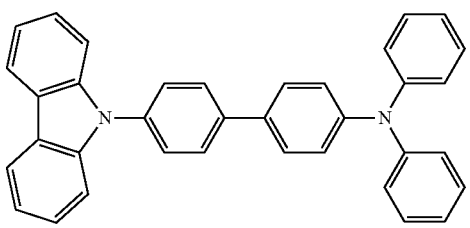

-continued
HT17
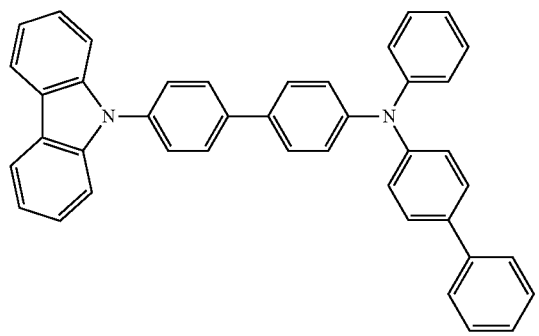
HT18
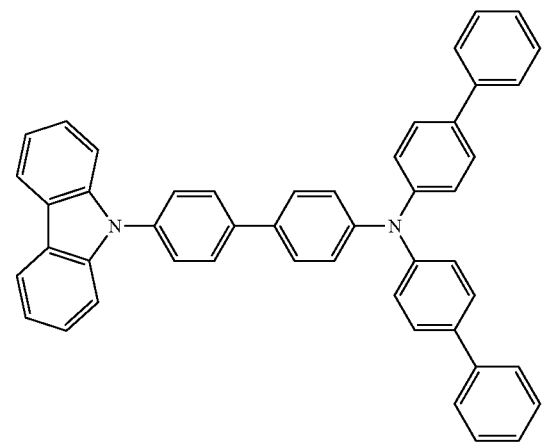
HT19
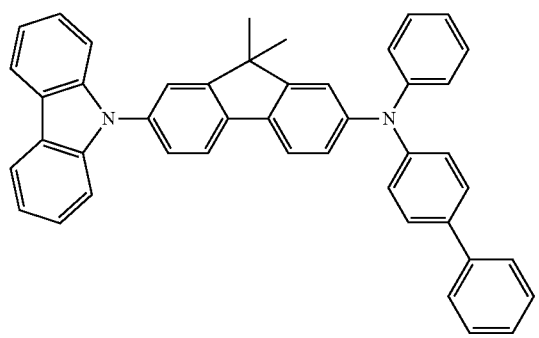
HT20
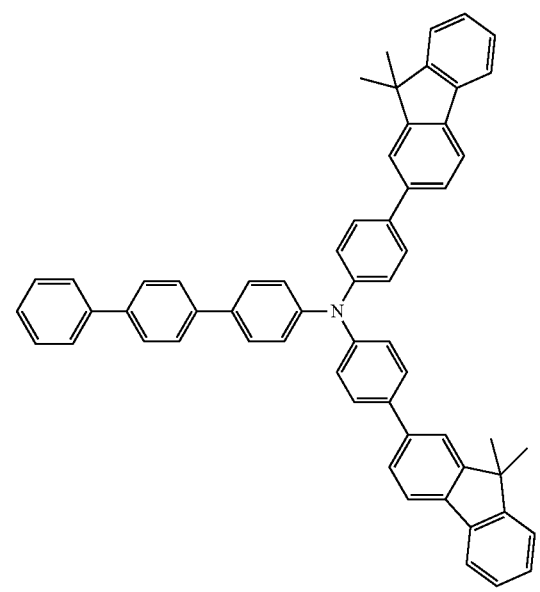

-continued
HT21
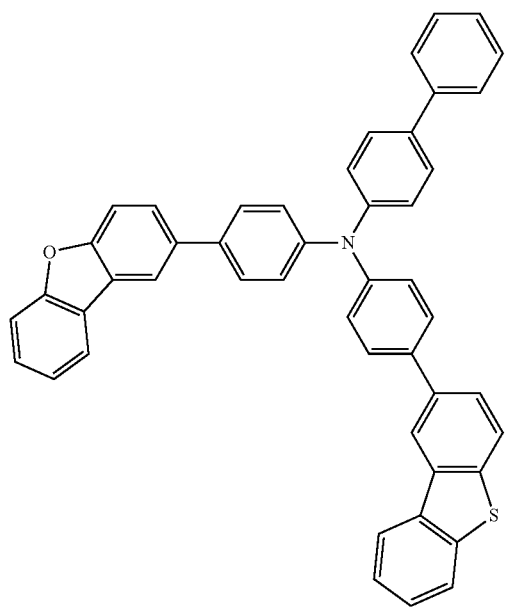
HT22
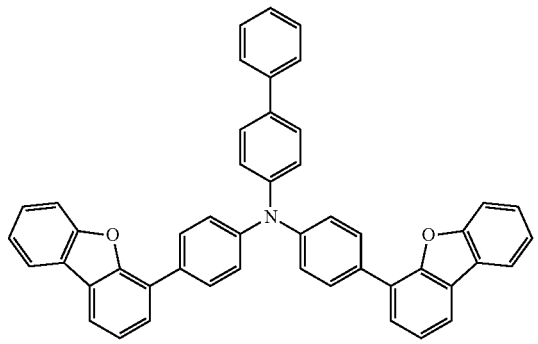
HT23
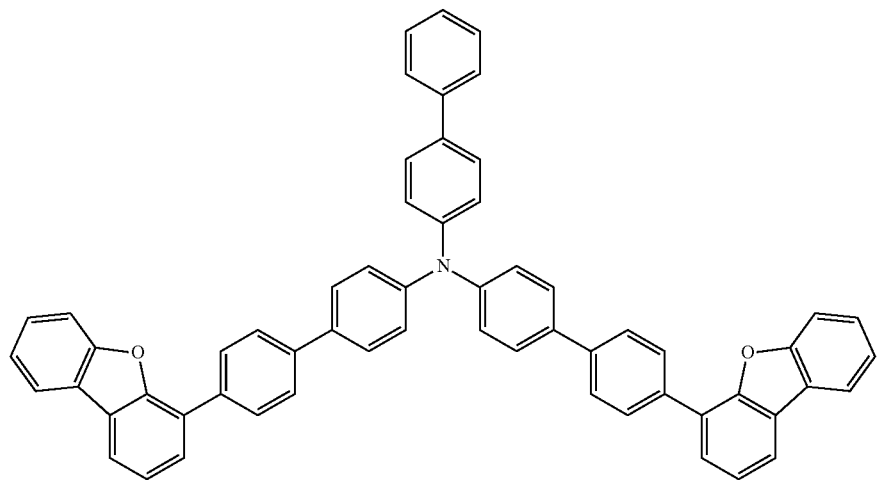
HT24
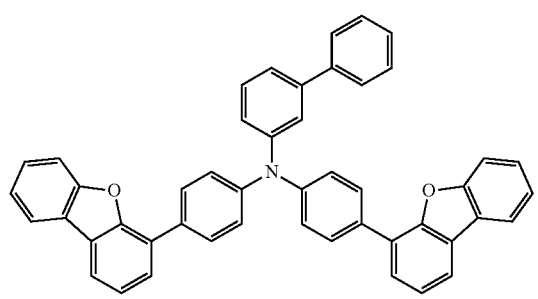
HT25
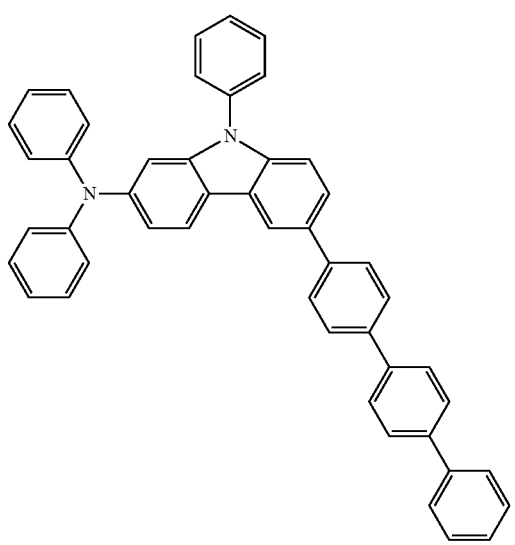

-continued
HT26
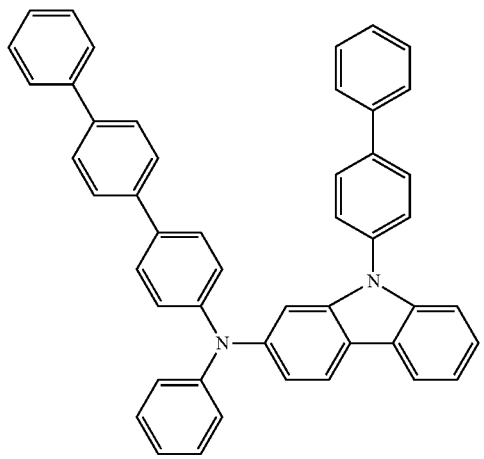
HT27
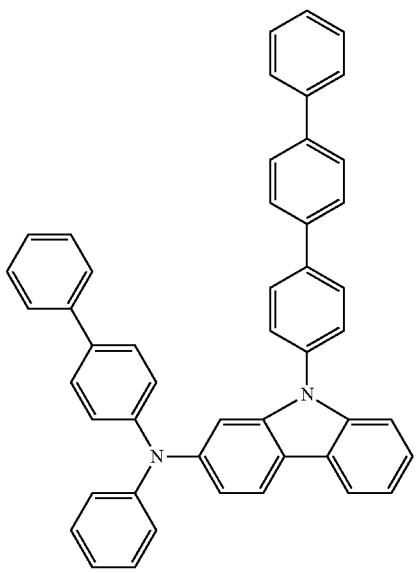
HT28
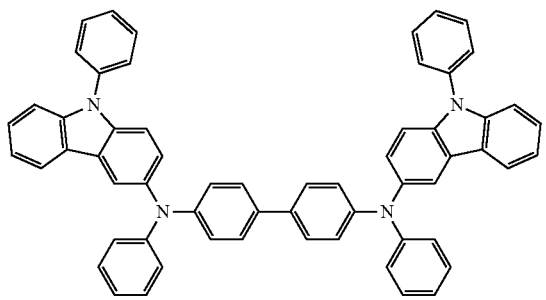
HT29
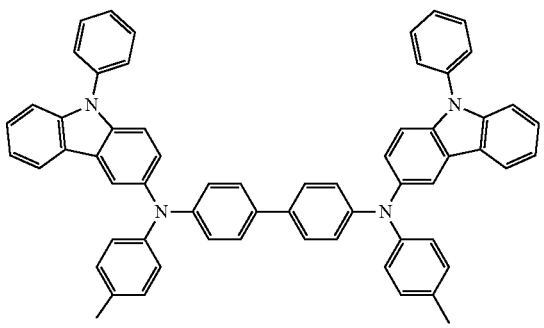
HT30
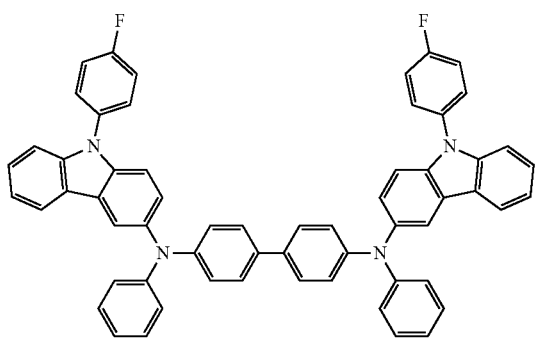
HT31
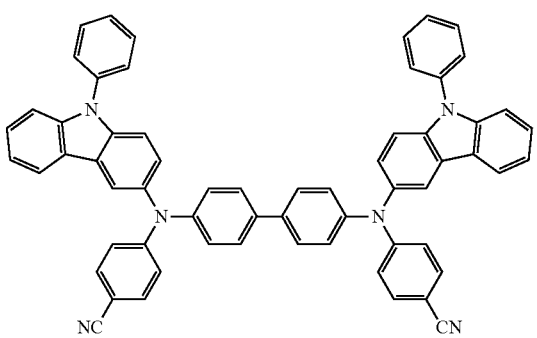

-continued
HT32
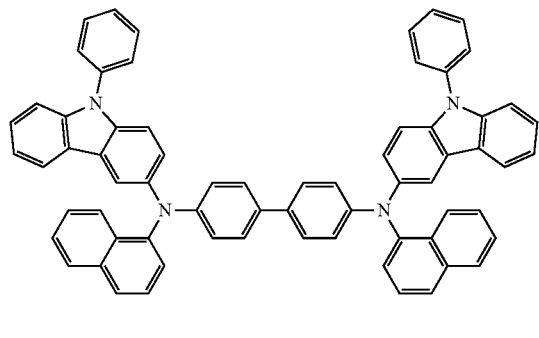
HT33
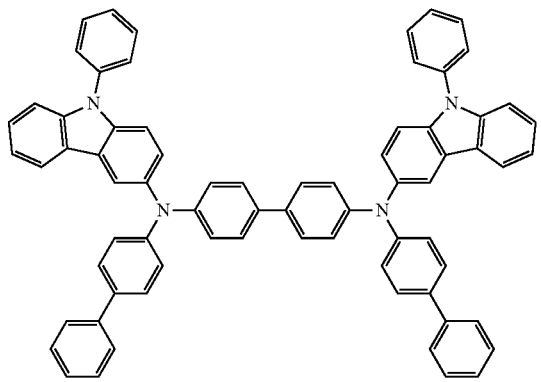
HT34
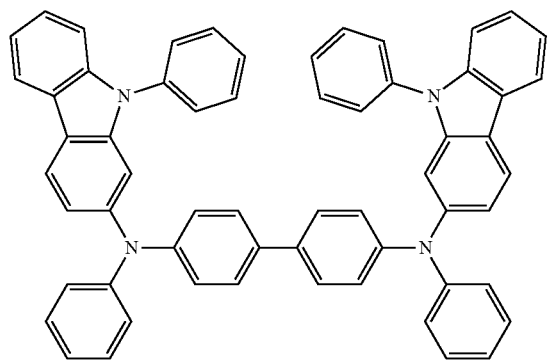
HT35
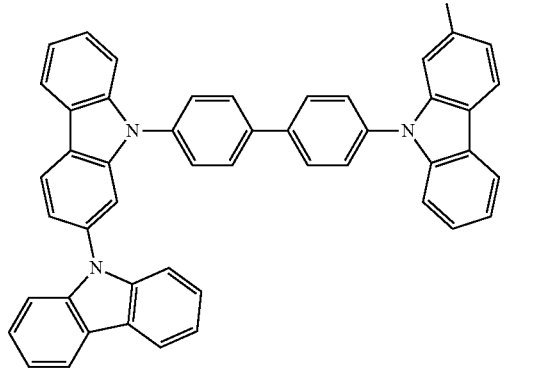
HT36
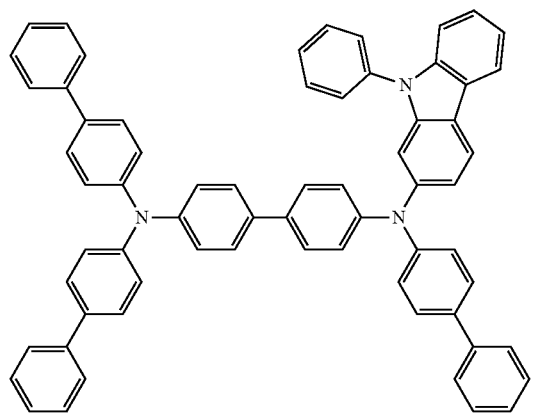
HT37
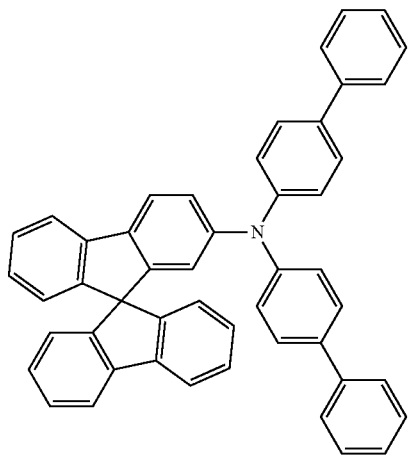

HT38
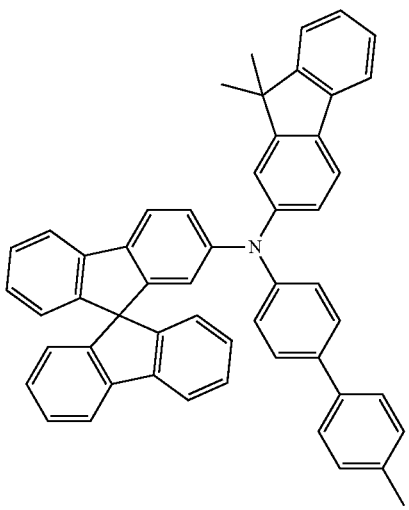

HT39
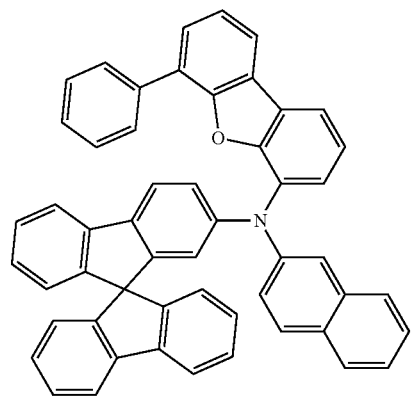

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer and the hole transport layer are within any of the foregoing ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[p-Dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one or more embodiments, a lowest unoccupied molecular orbital (LUMO) of the p-dopant may be −3.5 eV or less.

The p-dopant may include, in addition to the borole compound represented by Formula 1, at least one selected from a quinone derivative, a metal oxide, and a cyano group-containing compound, but embodiments of the present disclosure are not limited thereto.

For example, the p-dopant may include, in addition to the borole compound represented by Formula 1, a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221 below:

but embodiments of the present disclosure are not limited thereto:

HAT-CN
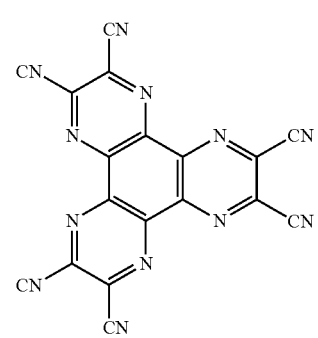

F4-TCNQ
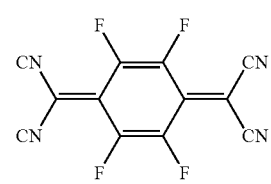

Formula 221
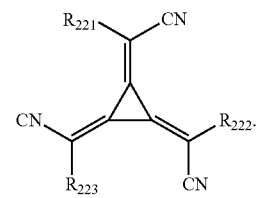

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single (or sole) layer to emit white light.

The emission layer may include a host and a dopant. The dopant may include at least one selected from a phosphorescent dopant and a fluorescent dopant.

An amount of the dopant in the emission layer may be, in general, in a range of about 0.01 parts to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within any of the foregoing ranges, excellent light-emission characteristics may be obtained without a substantial increase in driving voltage.

[Host in Emission Layer]

In one or more embodiments, the host may include a compound represented by Formula 301 below.

<Formula 301>

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one or more embodiments, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more Ar301(s) may be linked via a single bond.

In one or more embodiments, the compound represented by Formula 301 may be represented by Formula 301-1 or 301-2:

Formula 301-1

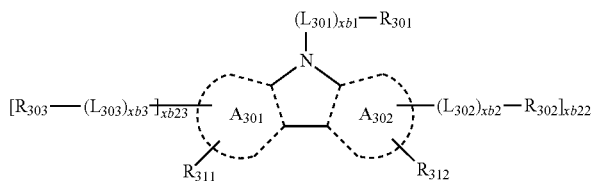

Formula 301-2

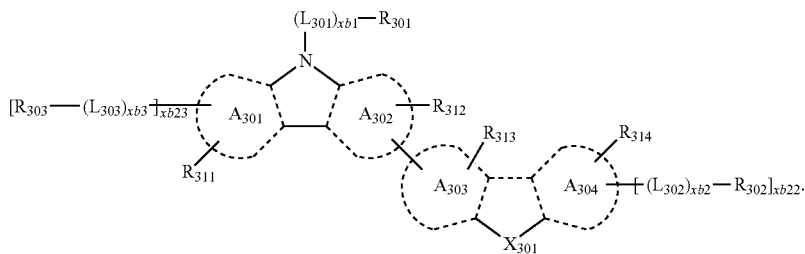

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si$(Q_{31})(Q_{32})(Q_{33})$, —N$(Q_{31})(Q_{32})$, —B$(Q_{31})(Q_{32})$, —C$(=O)(Q_{31})$, —S$(=O)_2(Q_{31})$, and —P$(=O)(Q_{31})(Q_{32})$, xb22 and xb23 may each independently be 0, 1, or 2, $L_{301}$, xb1, $R_{301}$, and $Q_{31}$ to $Q_{33}$ may be the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group;

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{31}$ to $Q_{33}$ may be the same as described above.

In one or more embodiments, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an aza carbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{31}$ and $Q_{33}$ may be the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

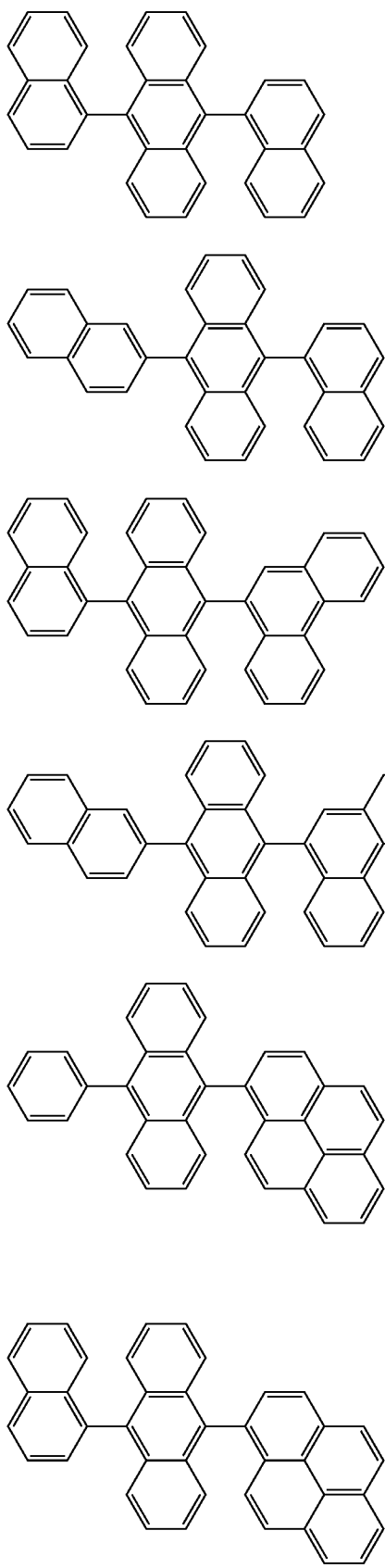
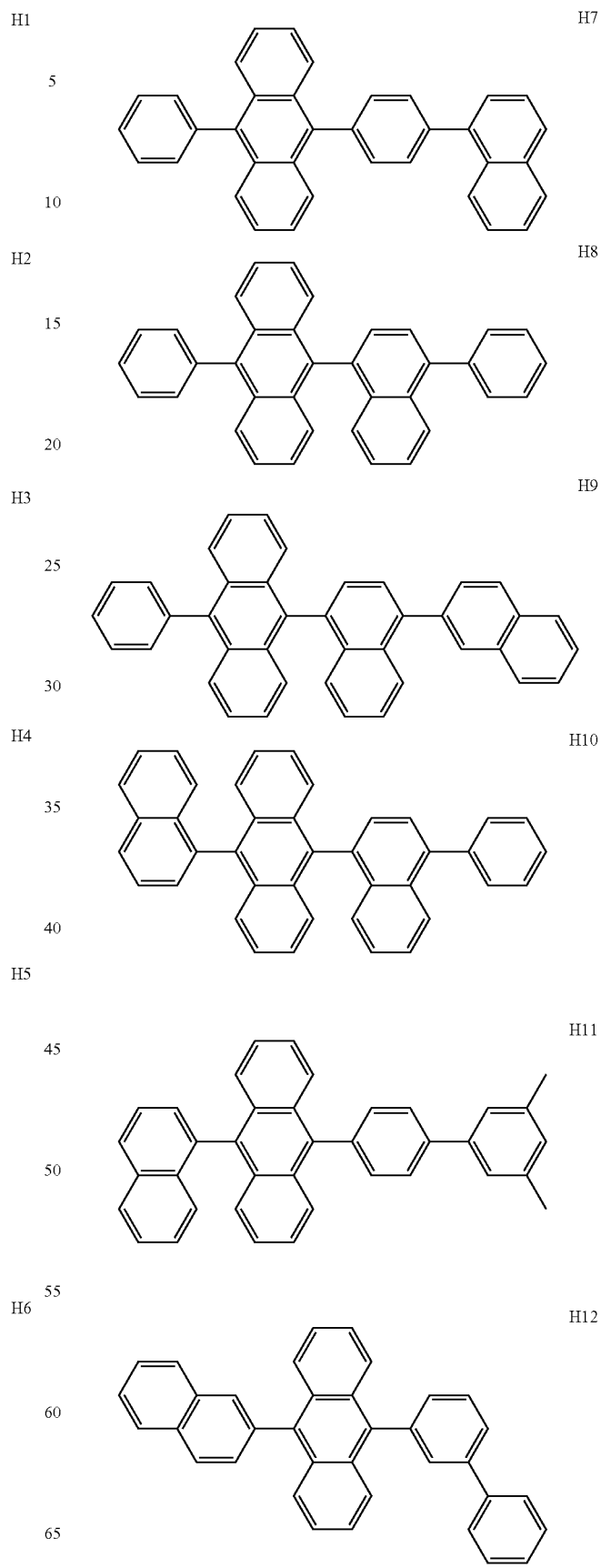

H13
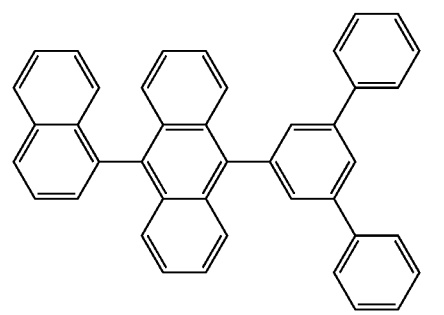
H14
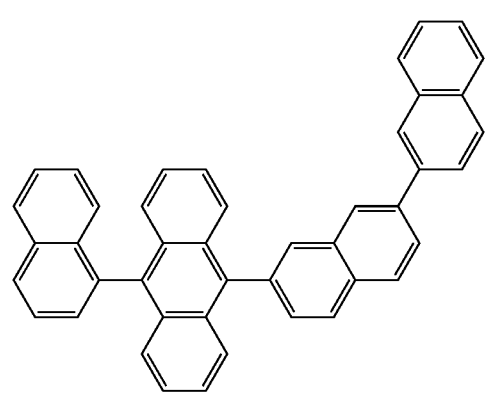
H15
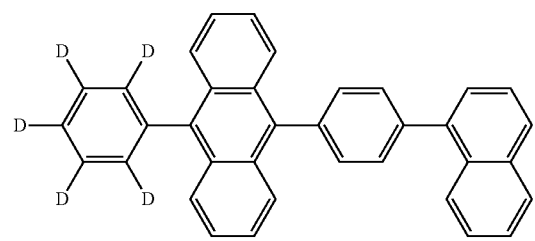
H16
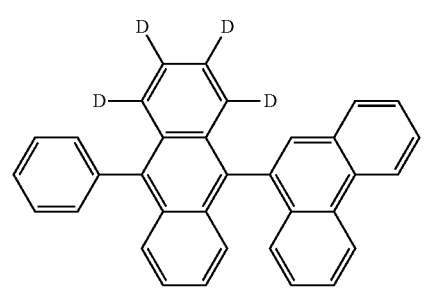
H17
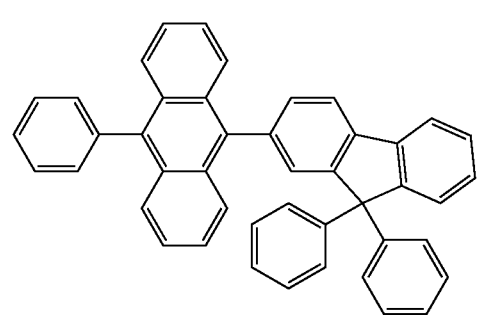
H18
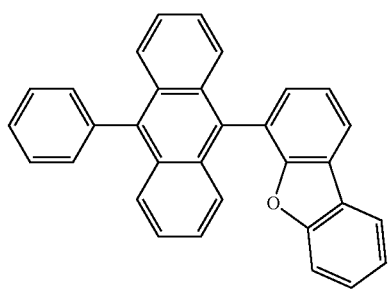
H19
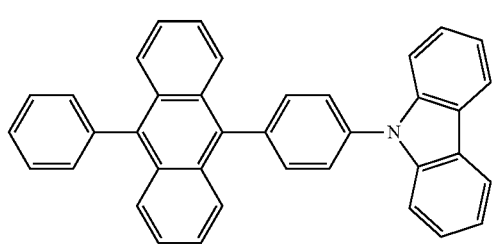
H20
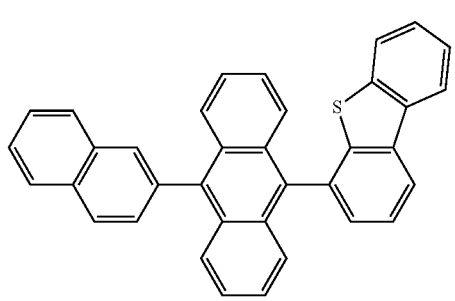
H21
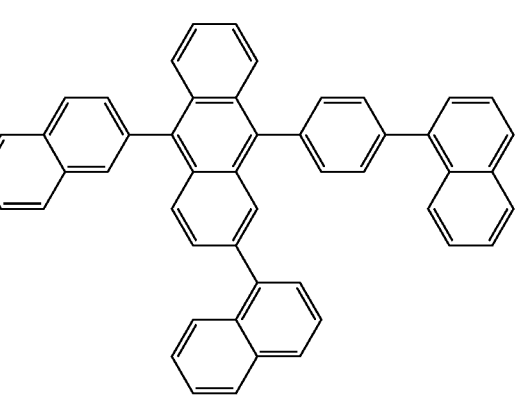
H22
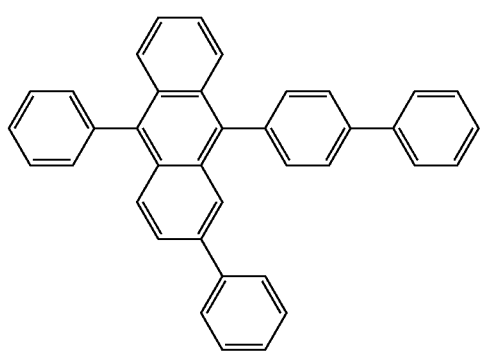

H23
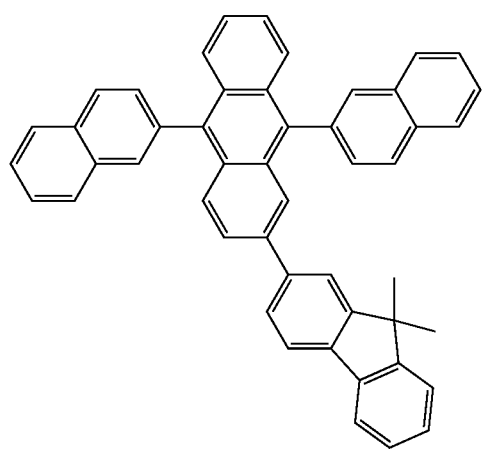
H24
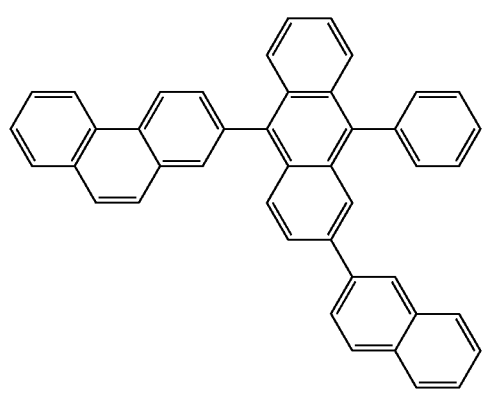
H25
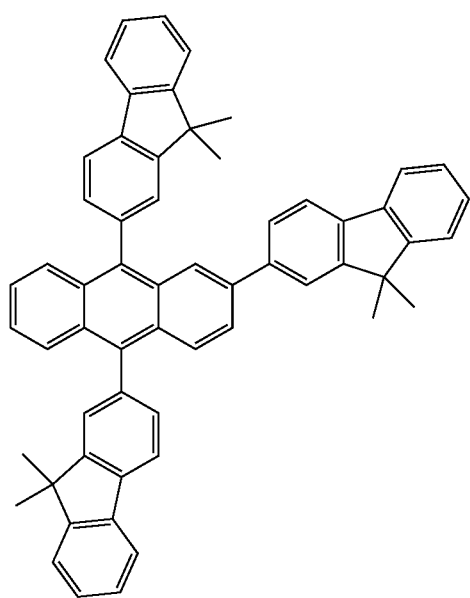
H26
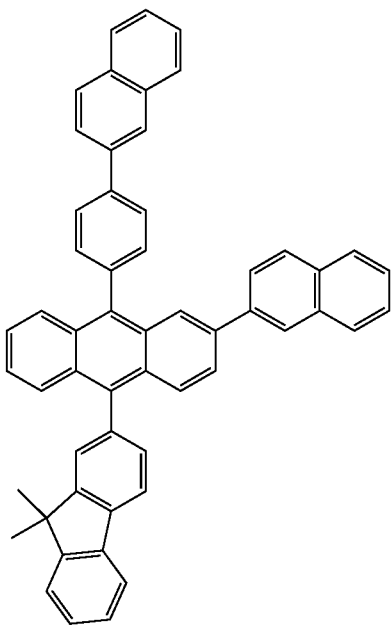
H27
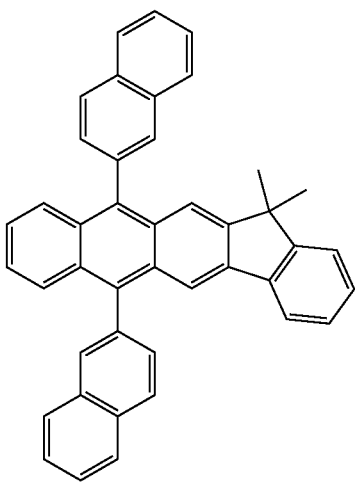
H28
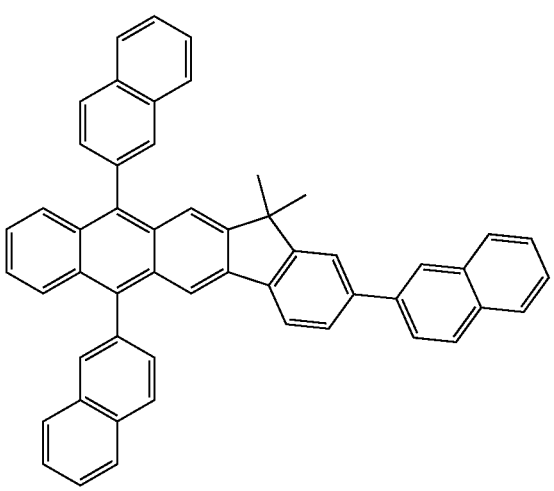

-continued
H29
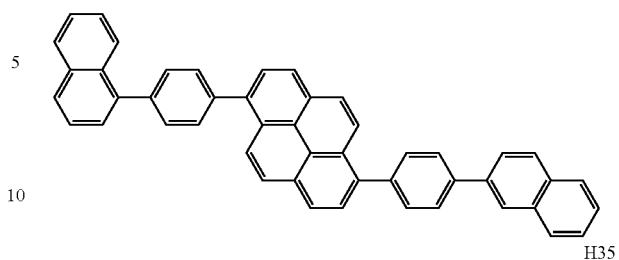
H30
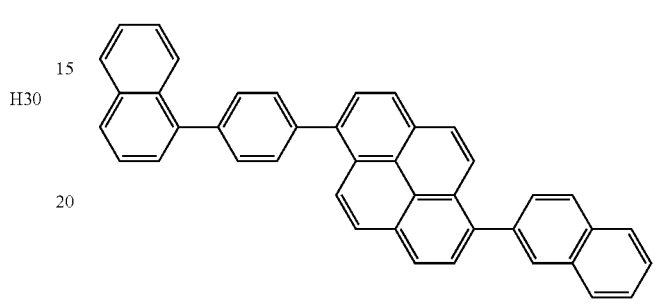
H31
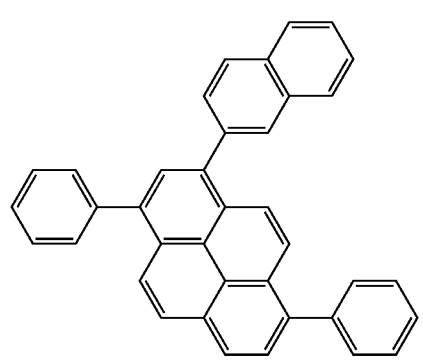
H32
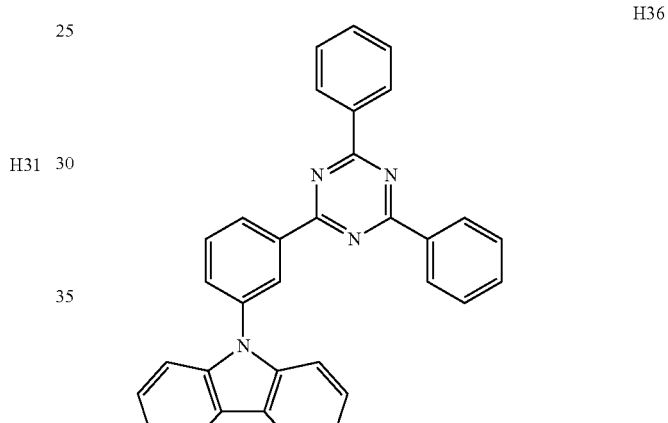
H33
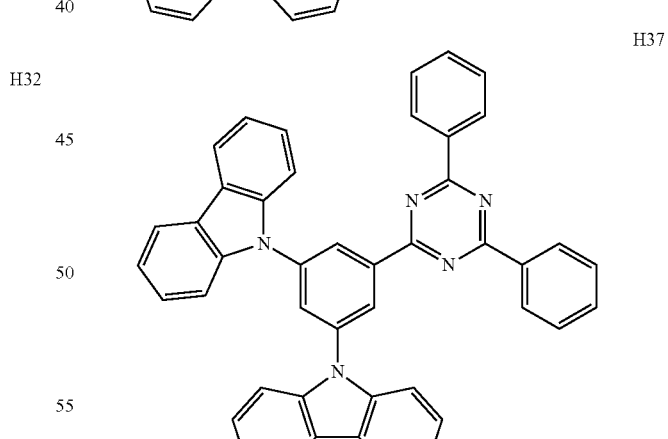
H34
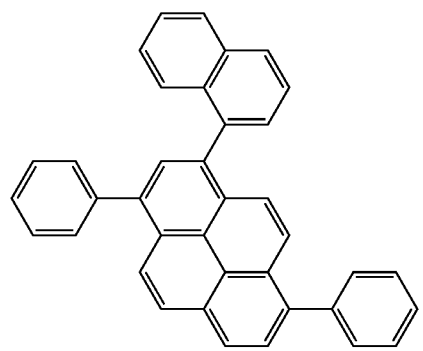
H35
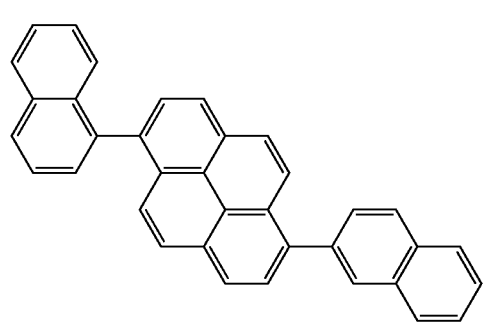
H36
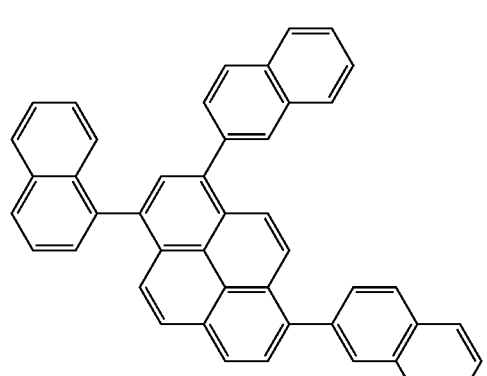
H37
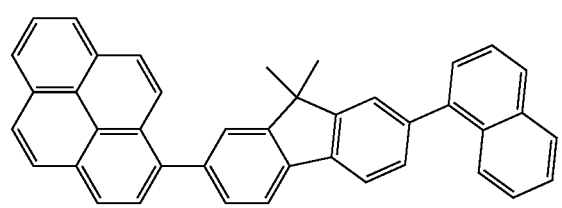
H38
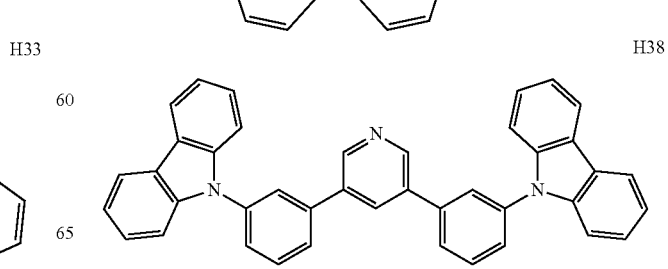

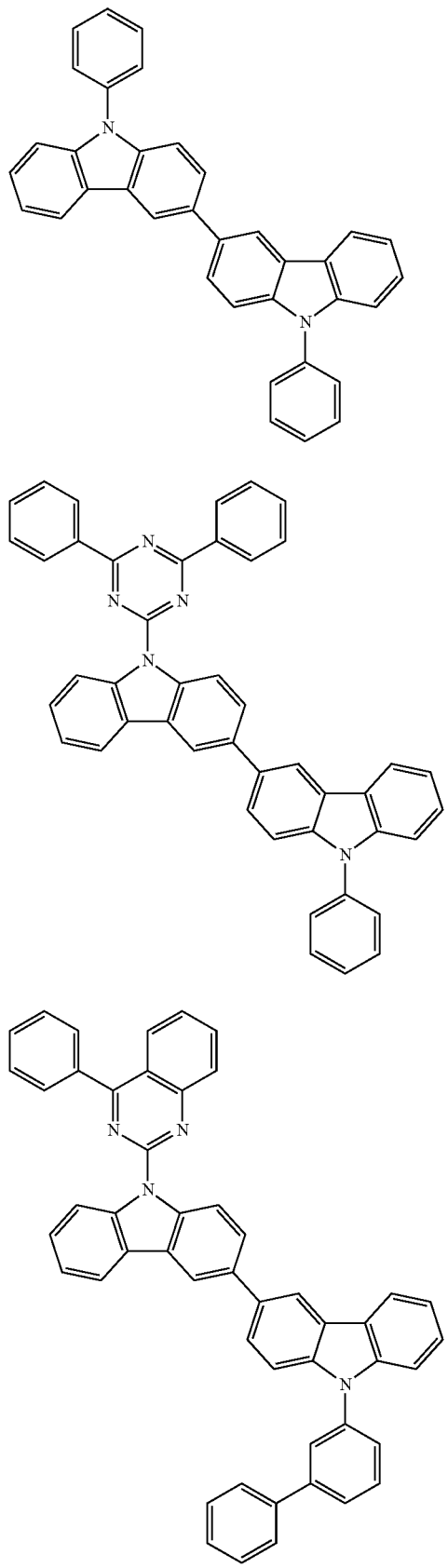
H39
H40
H41
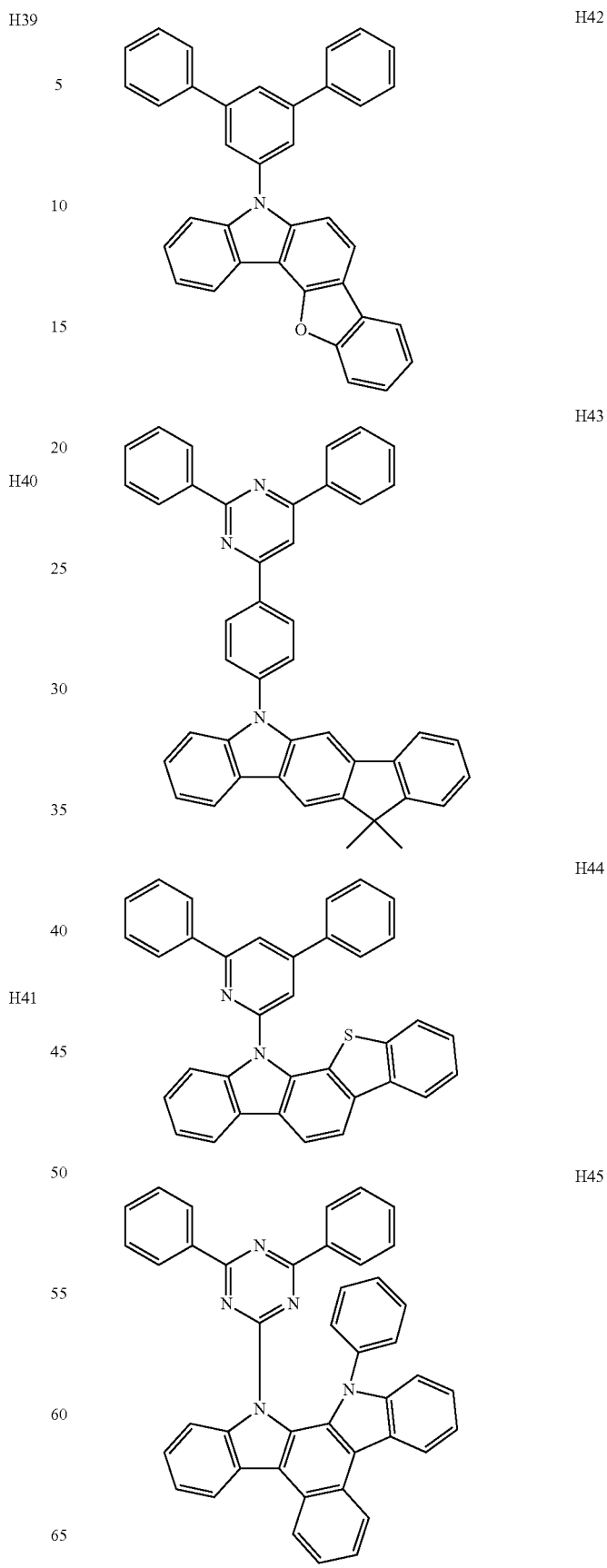
H42
H43
H44
H45

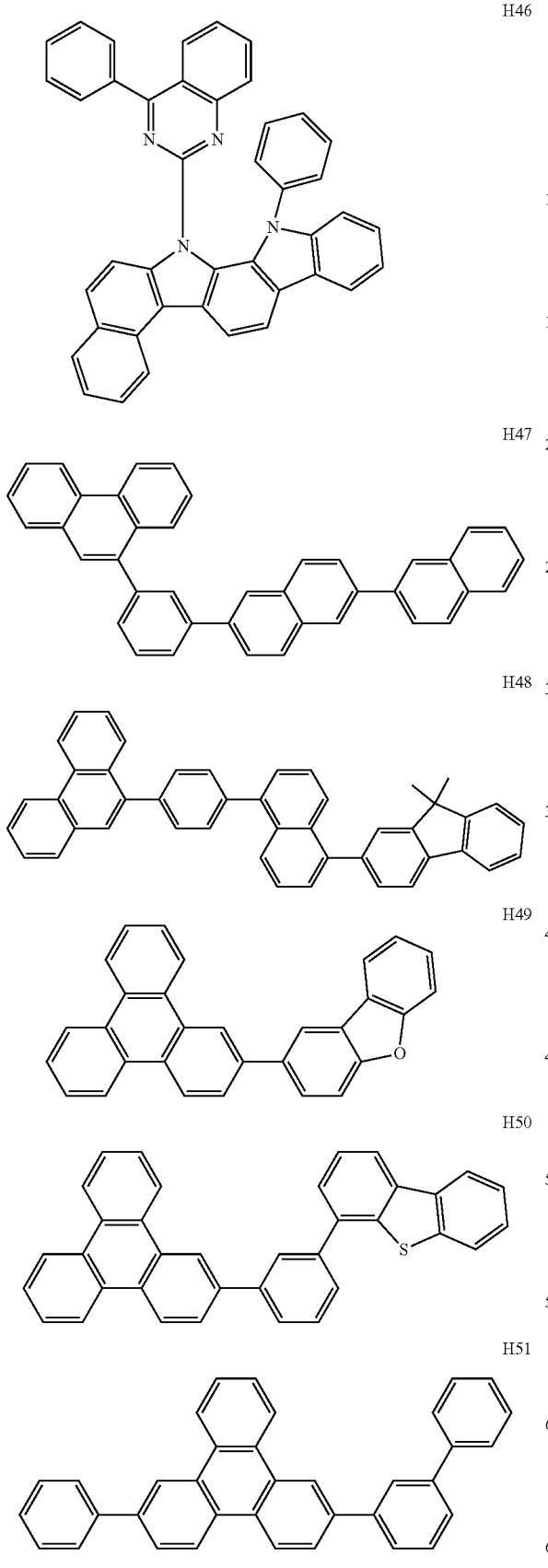
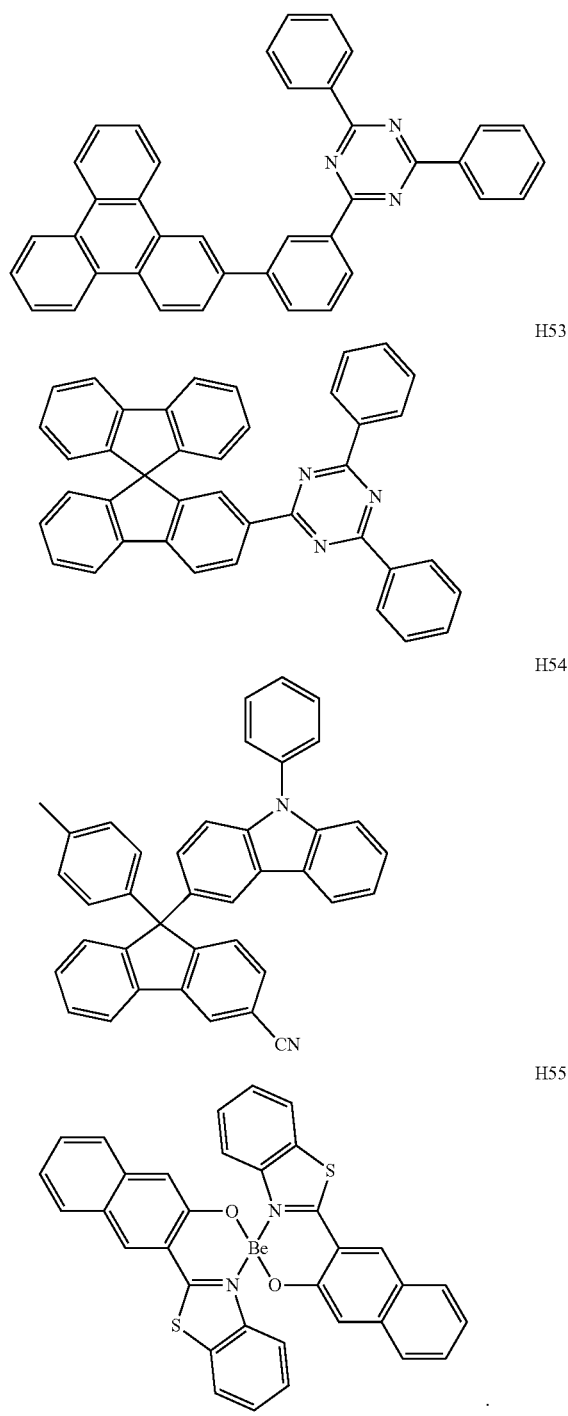
[Phosphorescent Dopant Included in Emission Layer in Organic Layer 150]
The phosphorescent dopant may include an organometallic complex represented by Formula 401 below:
$$M(L_{401})_{xc1}(L_{402})_{xc2} \quad \text{Formula 401}$$

-continued

Formula 402

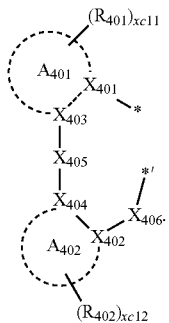

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ cyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, and xc11 and xc12 may each independently be an integer from 0 to 10,

* and *' in Formula 402 each indicate a binding site to M in Formula 401.

In one or more embodiments, $A_{401}$ and $A_{402}$ in Formula 402 may each independently be selected from a benzene group, a naphthalene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$); and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is two or more, two $A_{401}$(s) in 2 or more $L_{401}$(s) may optionally be linked via $X_{407}$, which is a linking group, or two $A_{402}$(s) in 2 or more $L_{401}$(s) may optionally be linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), a carboxylic acid (for example, picolinate), —C(=O), isonitrile, —CN, and phosphorus (for example, phosphine or phosphite), but embodiments of the present disclosure are not limited thereto.

In one or more embodiments, the phosphorescent dopant may be, for example, selected from Compounds PD1 to PD25, but embodiments of the present disclosure are not limited thereto:

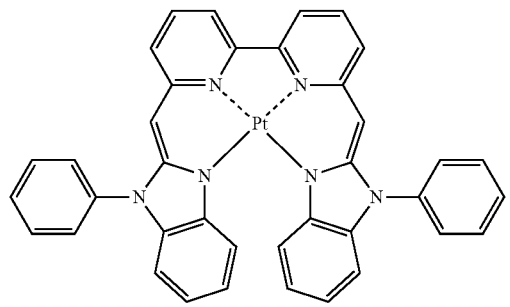

PD1

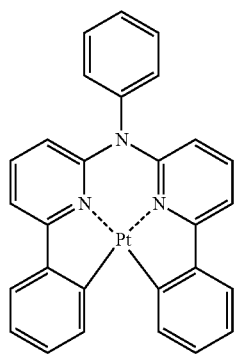

PD2

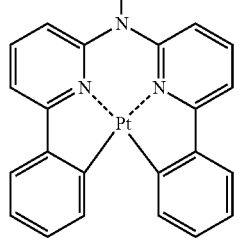

PD3

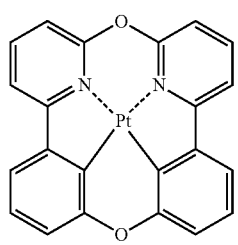

-continued

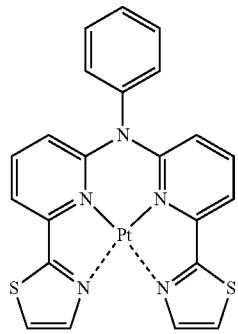

PD4

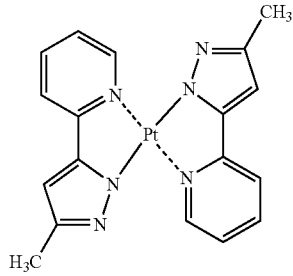

PD5

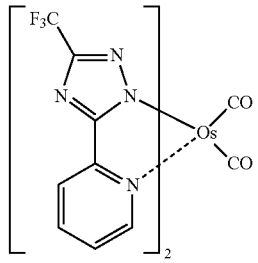

PD6

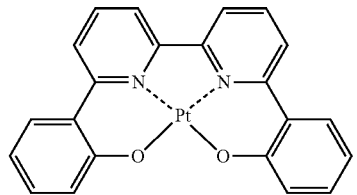

PD7

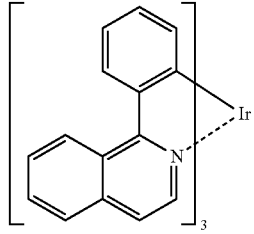

PD8

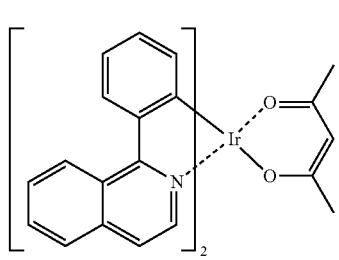

PD9

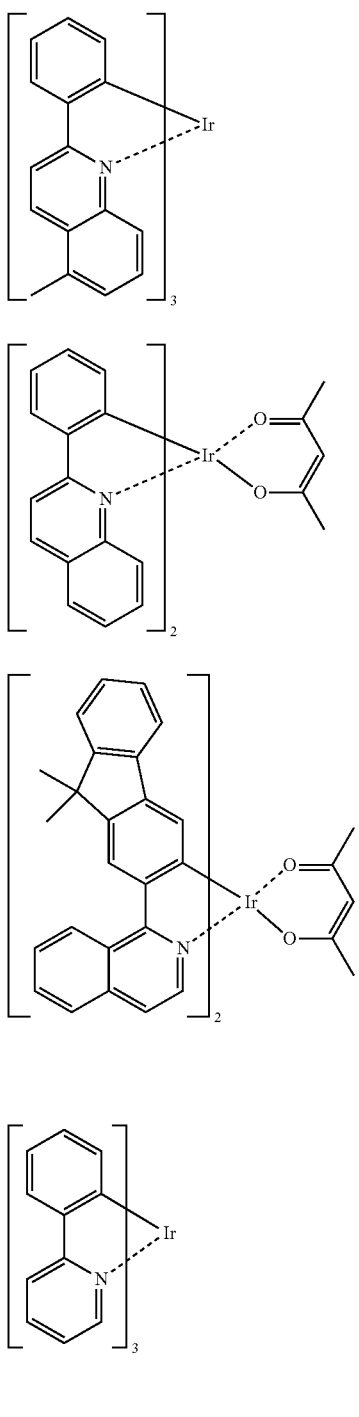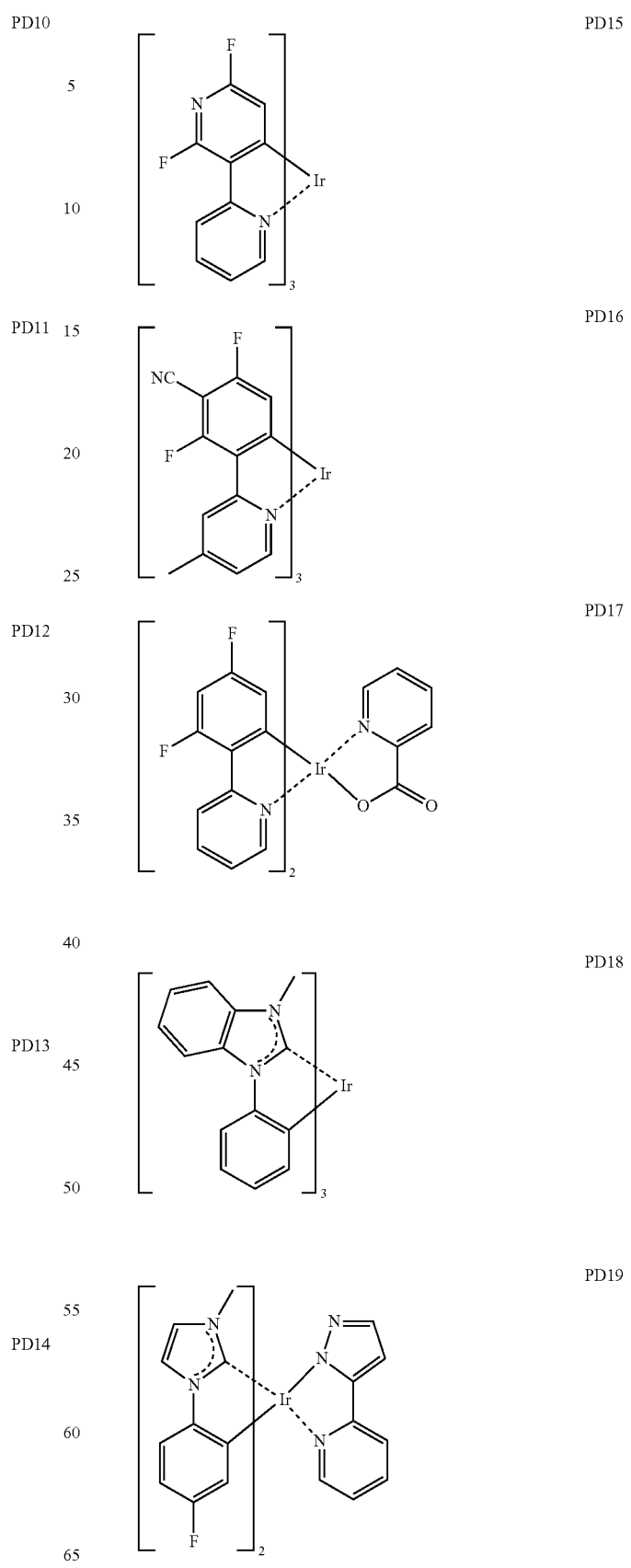

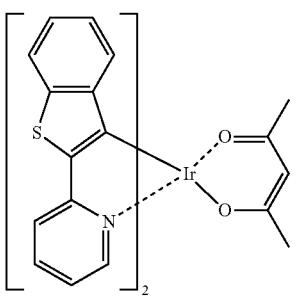
PD20

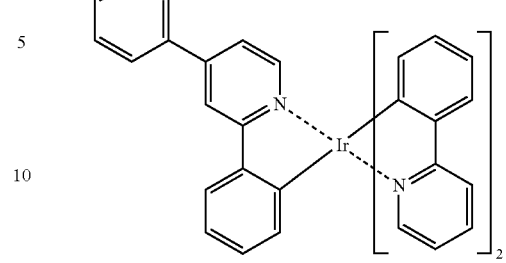
PD24

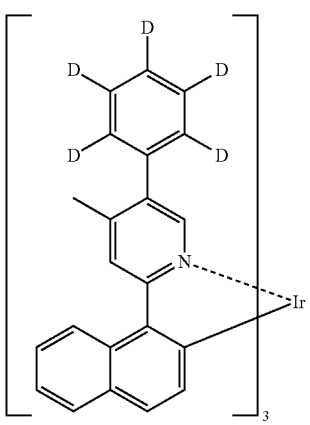
PD21

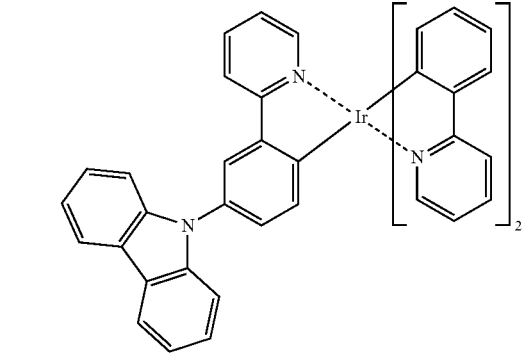
PD25

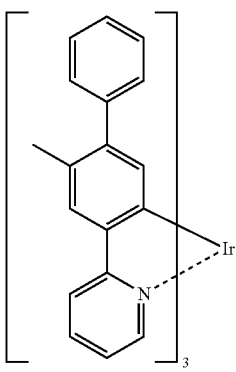
PD22

[Fluorescent Dopant in Emission Layer]

The fluorescent dopant may include an arylamine compound or a styrylamine compound.

The fluorescent dopant may include a compound represented by Formula 501:

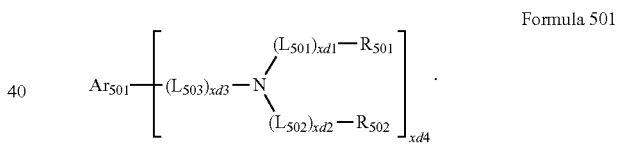

Formula 501

In Formula 501,

Ar$_{501}$ may be a substituted or unsubstituted C$_5$-C$_{60}$ carbocyclic group or a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, R$_{501}$ and R$_{502}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substi-

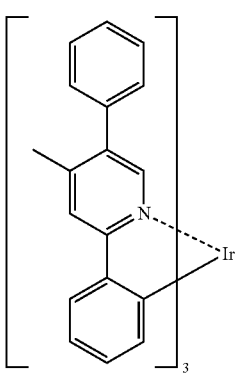
PD23 tuted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one or more embodiments, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:

FD1 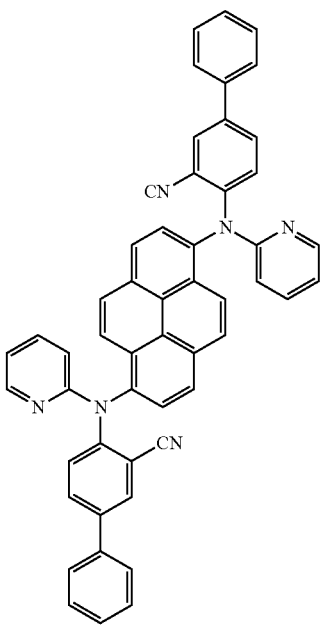
FD2 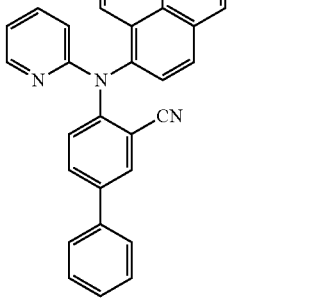
FD3 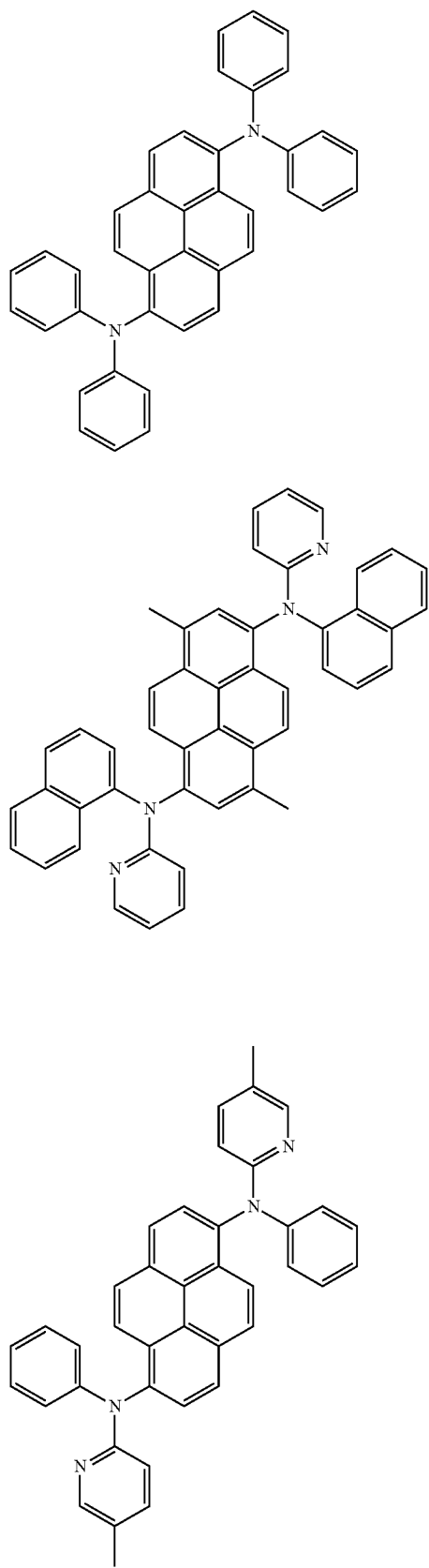
FD4 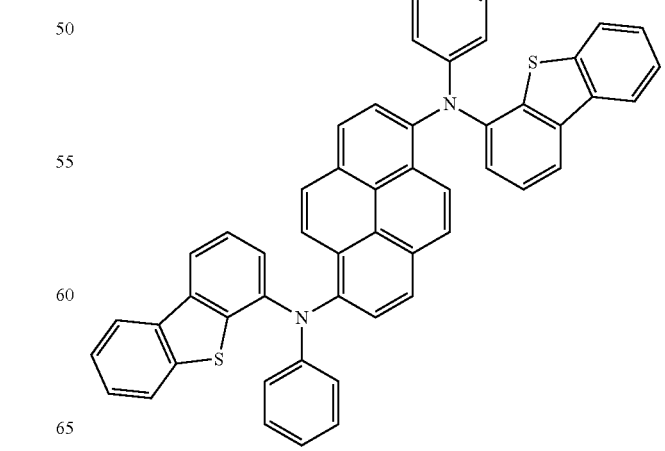
FD5
FD6

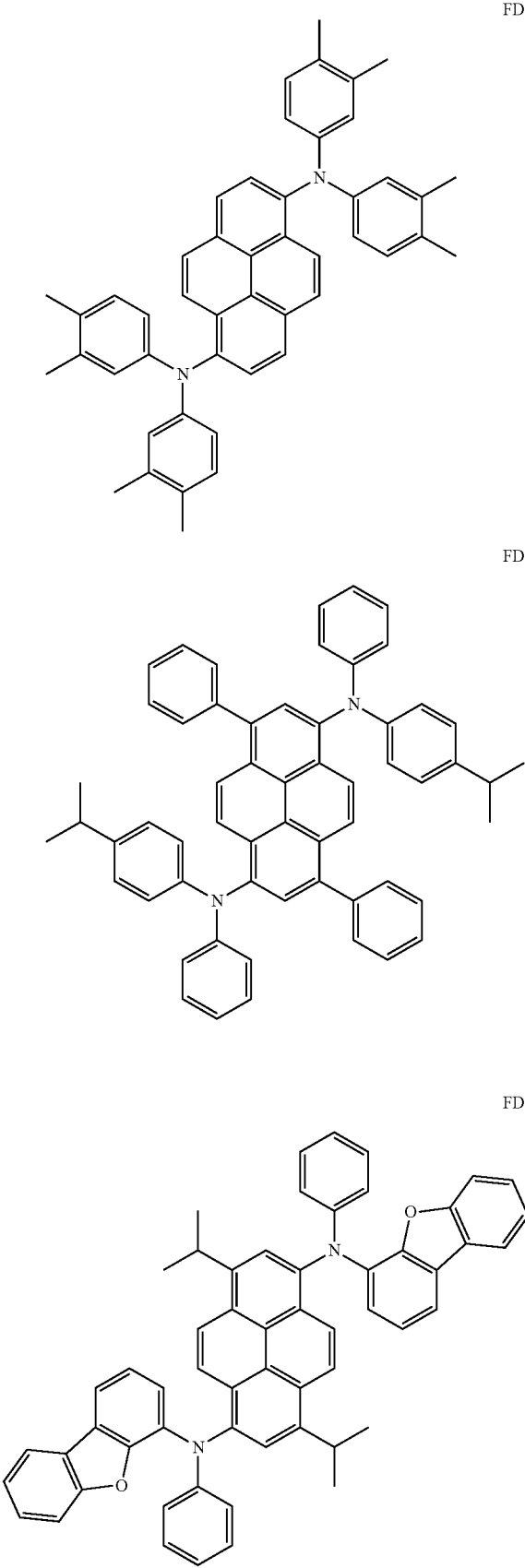
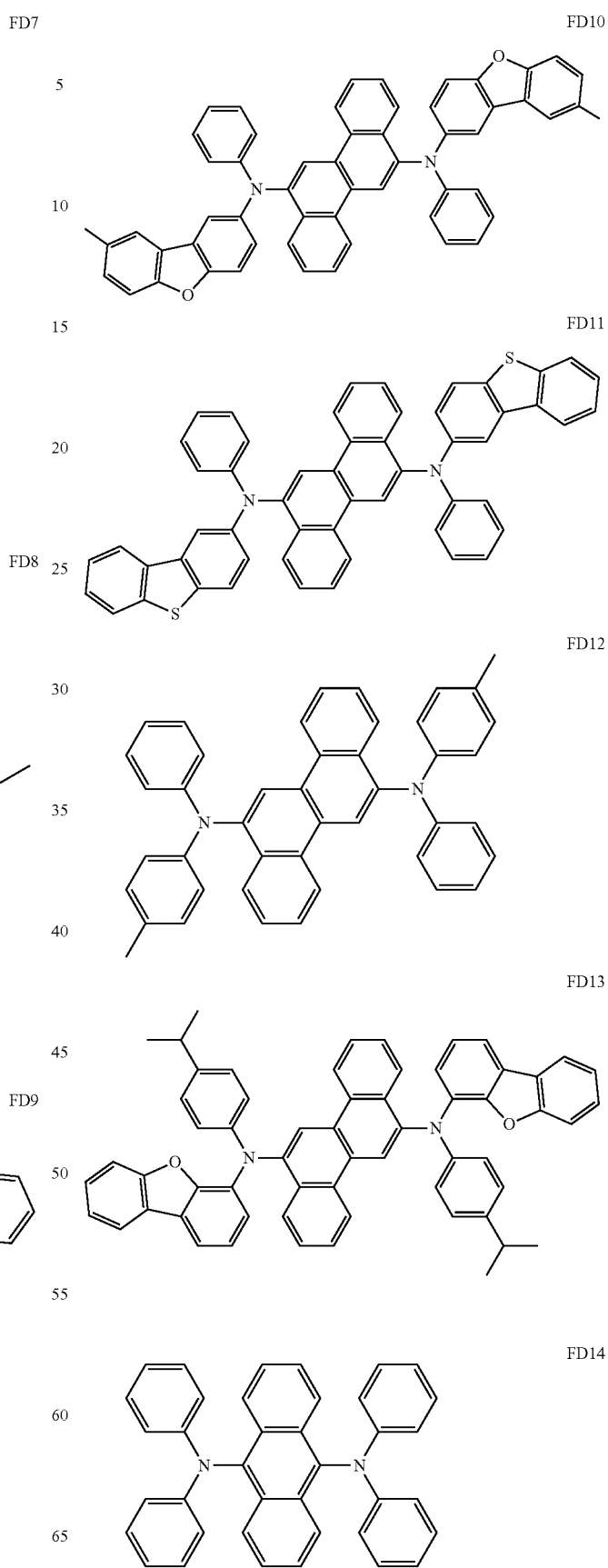

FD15
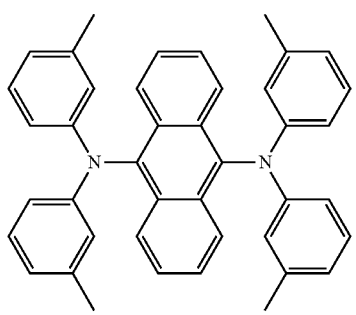
FD16
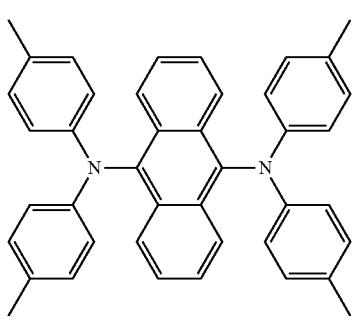
FD17
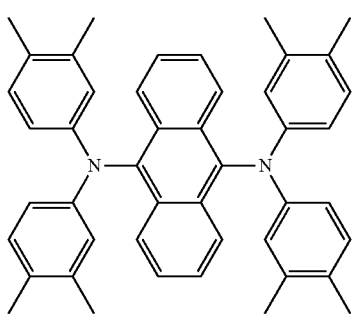
FD18
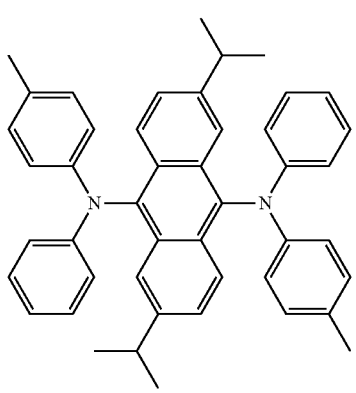
FD19
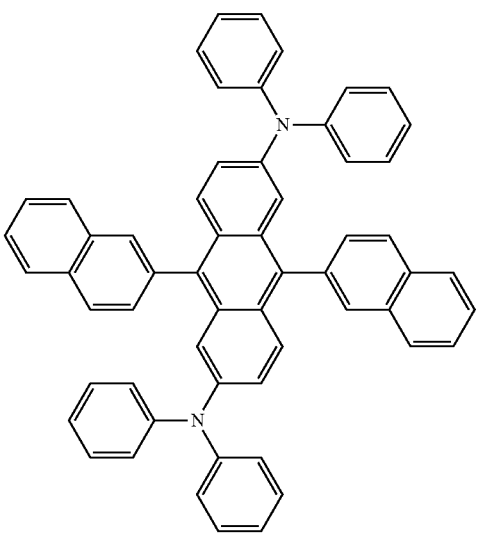
FD20
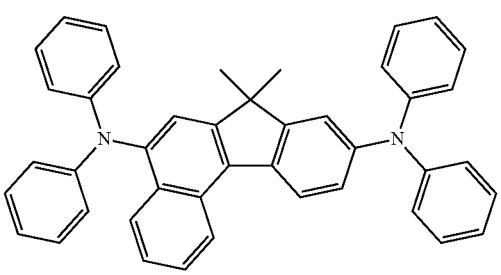
FD21
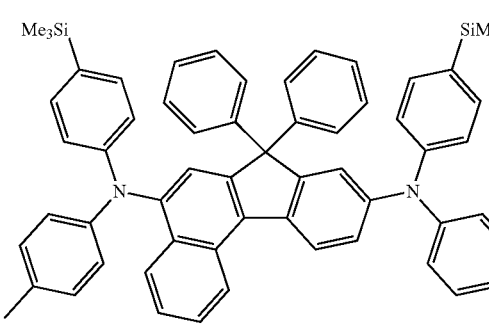
FD22
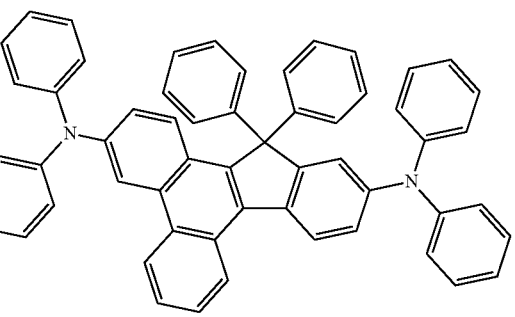
In one or more embodiments, the fluorescent dopant may be selected from the following compounds, but embodiments of the present disclosure are not limited thereto.

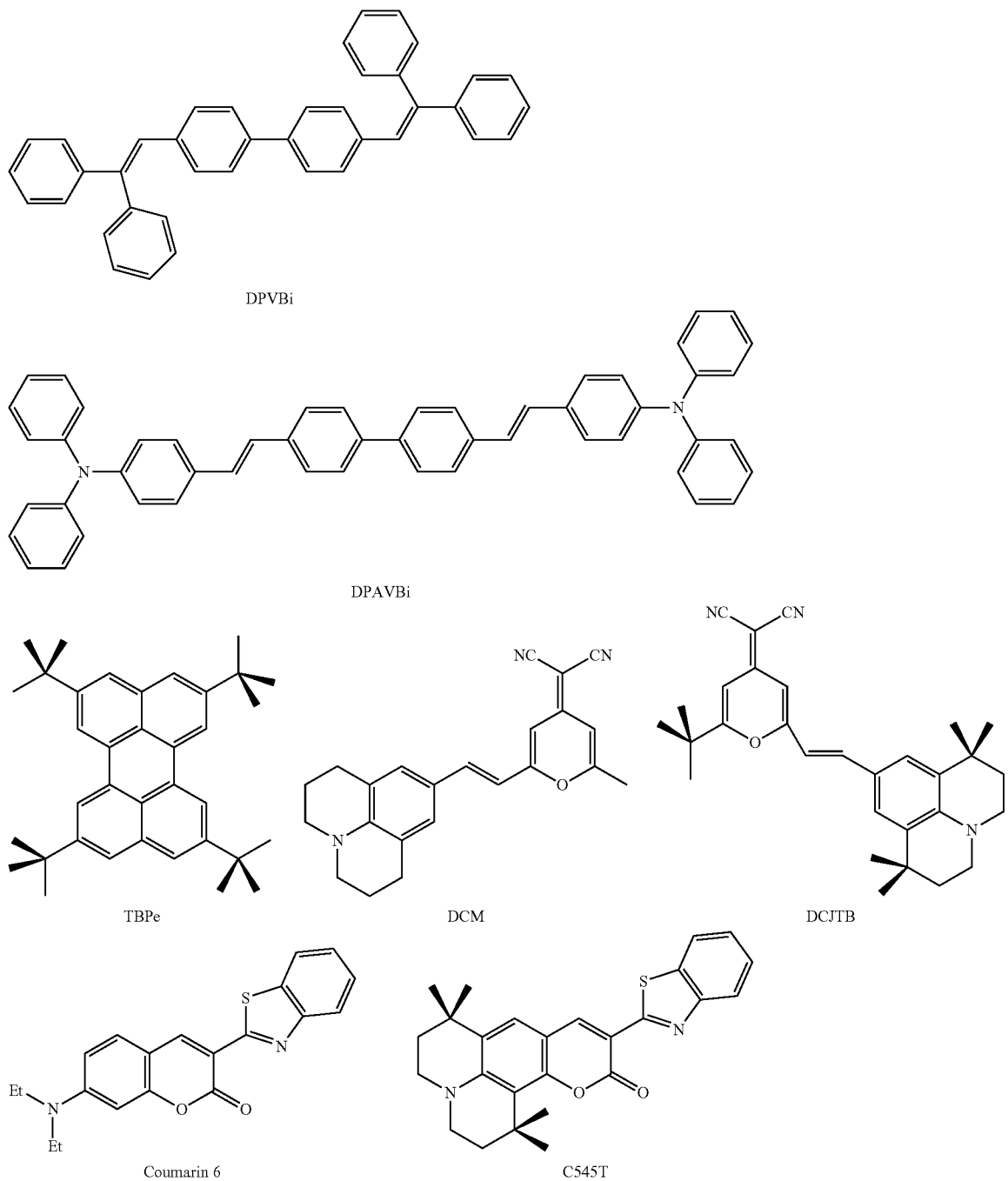

[Electron Transport Region in Organic Layer 150]

The electron transport region may have i) a single-layered structure including a single (or sole) layer including a single (or sole) material, ii) a single-layered structure including a single (or sole) layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

As used herein, the expression "π electron-depleted nitrogen-containing ring" refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

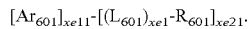   <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one or more embodiments, at least one of $Ar_{601}$(S) in the number of xe11 and $R_{601}$(S) in the number of xe21 may include the π electron-depleted nitrogen-containing ring.

In one or more embodiments, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, thiadiazol group, an imidazopyridine group, an imidazopyrimidine group, and an aza carbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1:

Formula 601-1

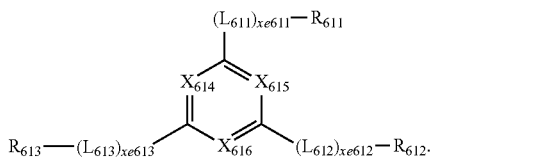

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

—S(=O)$_2$(Q$_{601}$) and —P(=O)(Q$_{601}$)(Q$_{602}$); and

Q$_{601}$ and Q$_{602}$ may be the same as described above.

The electron transport region may include at least one compound selected from Compounds ET1 to ET36, but embodiments of the present disclosure are not limited thereto:

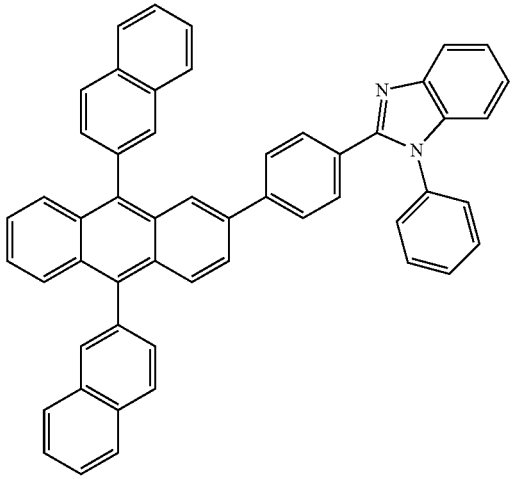

ET1

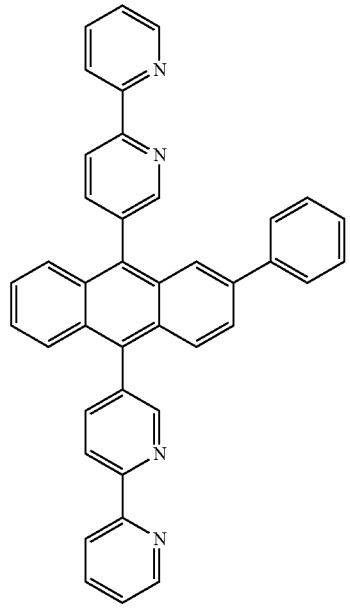

ET2

ET3
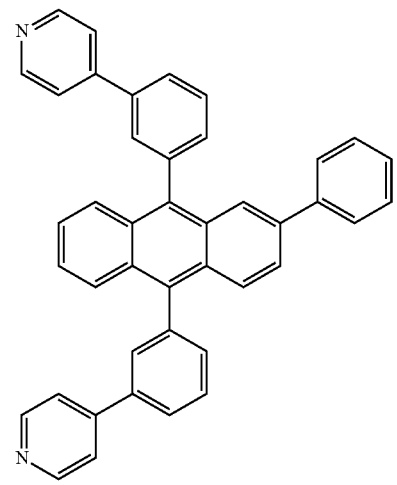
ET7
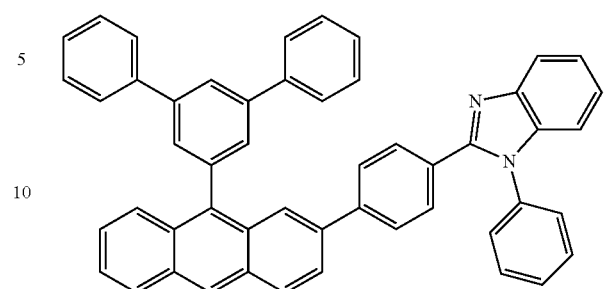
ET4
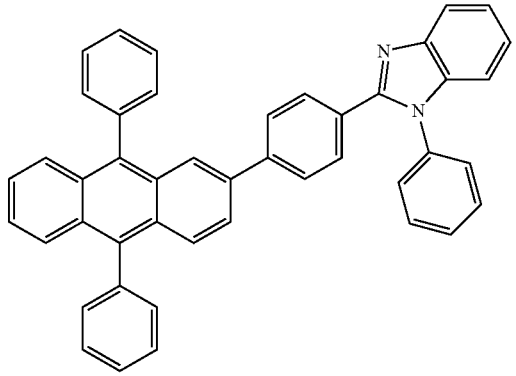
ET8
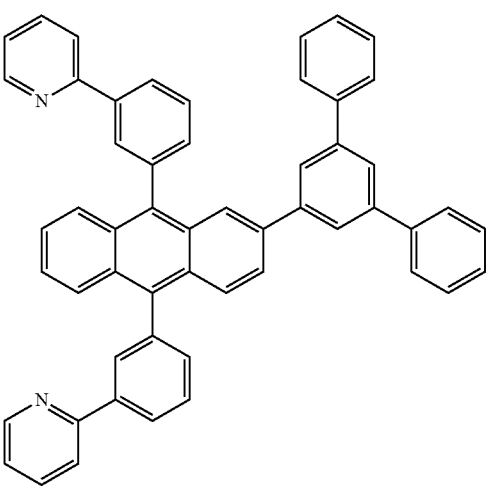
ET5
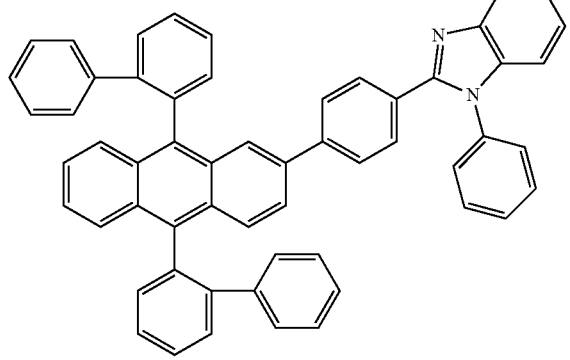
ET9
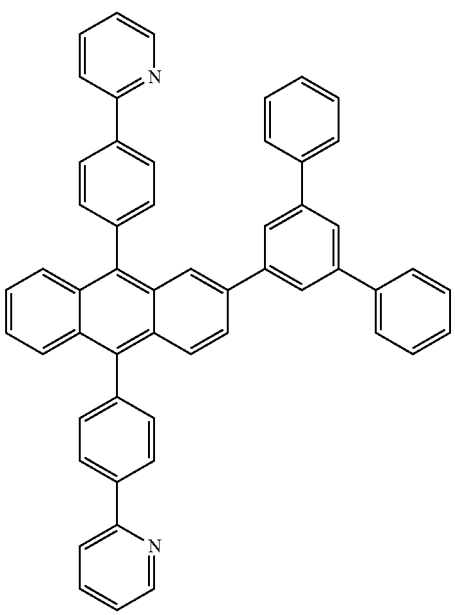
ET6
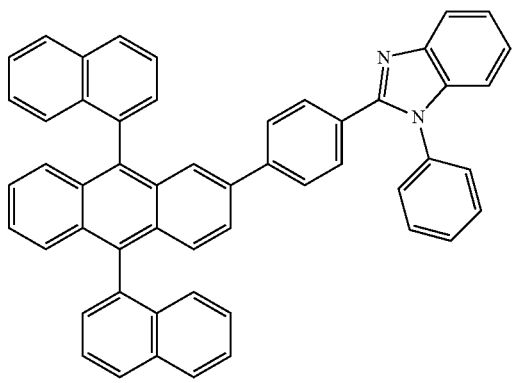

ET10
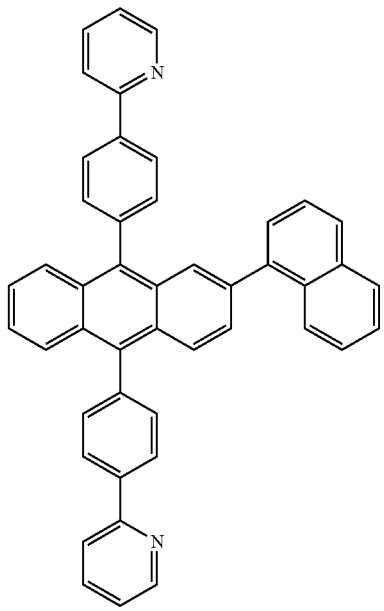
ET11
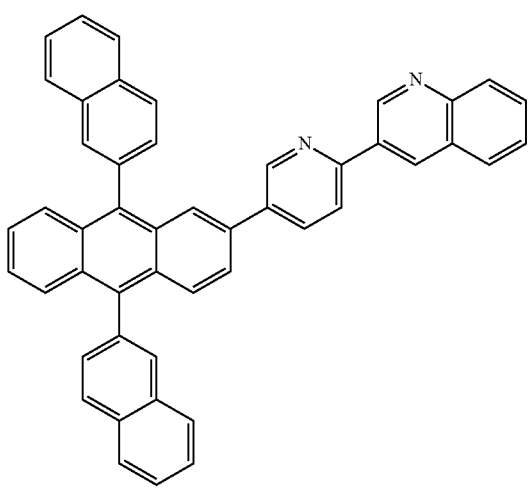
ET12
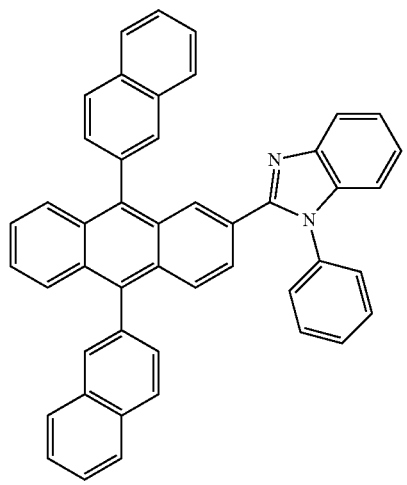
ET13
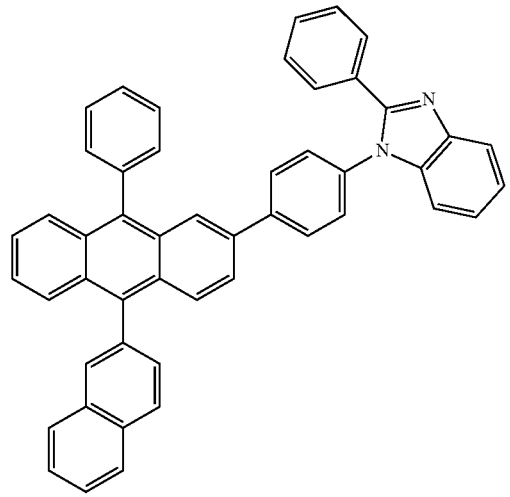
ET14
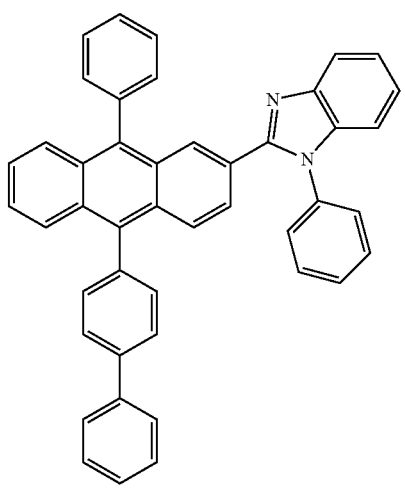
ET15
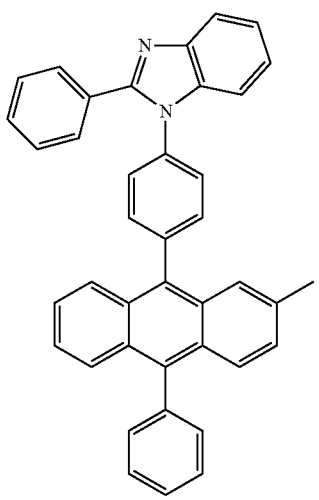

-continued
ET16
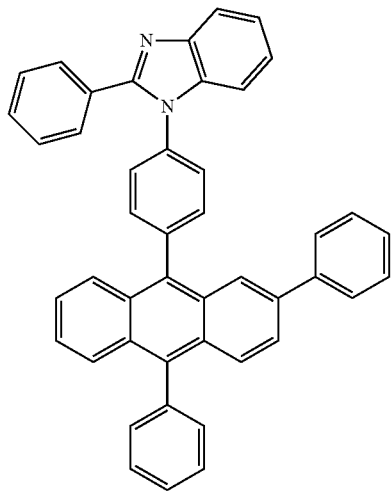
ET17
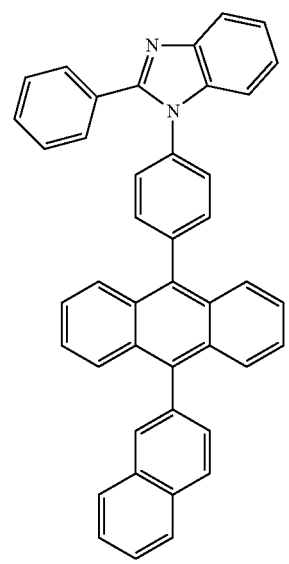
ET18
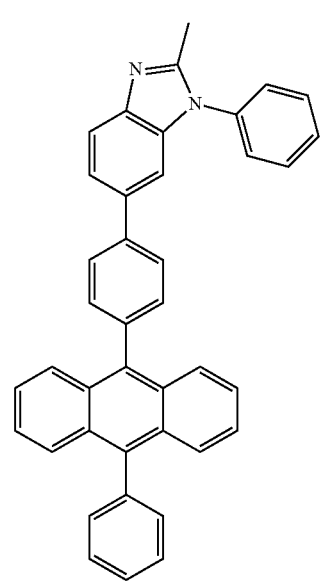
-continued
ET19
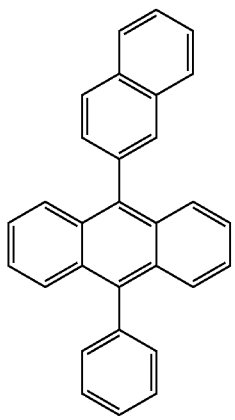
ET20
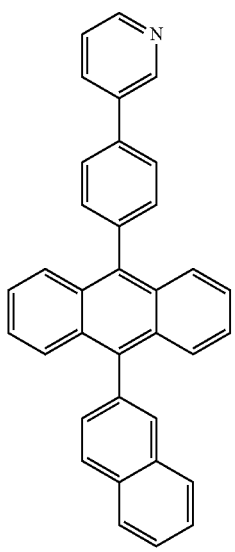
ET21
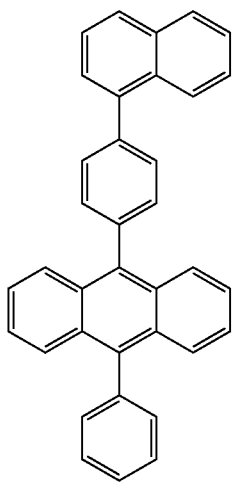

ET22
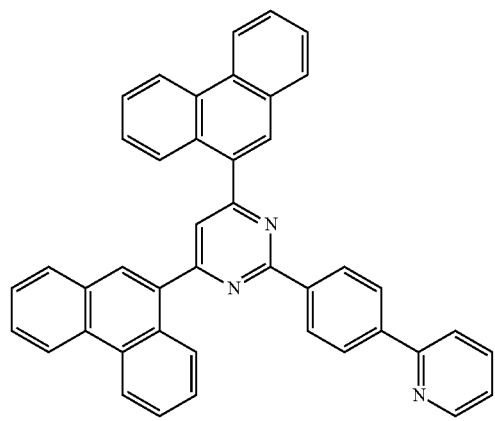
ET23
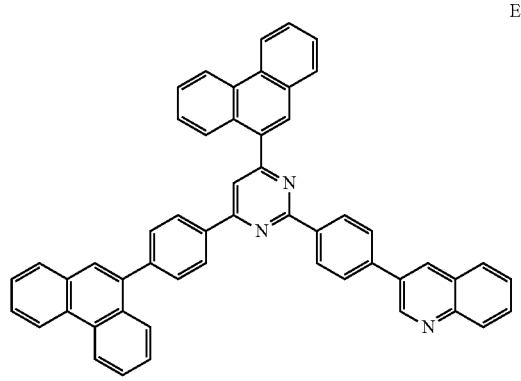
ET24
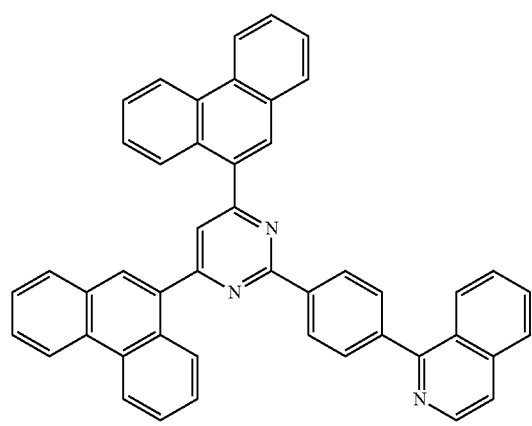
ET25
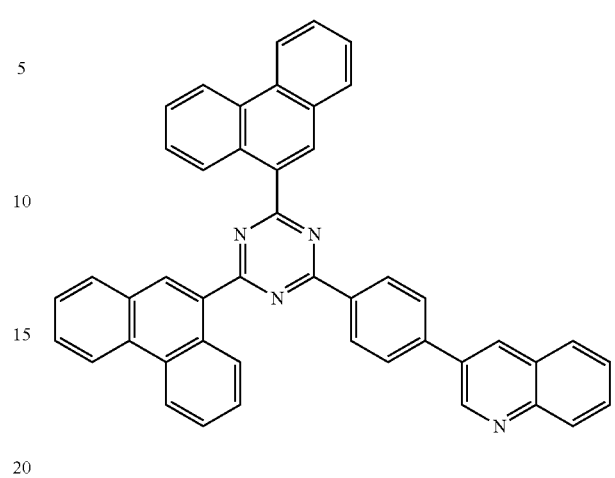
ET26
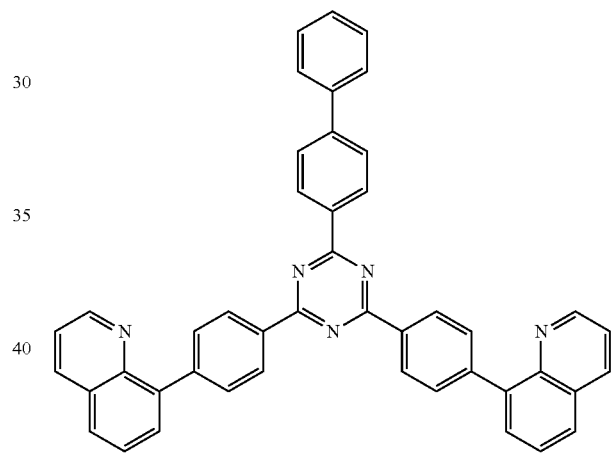
ET27
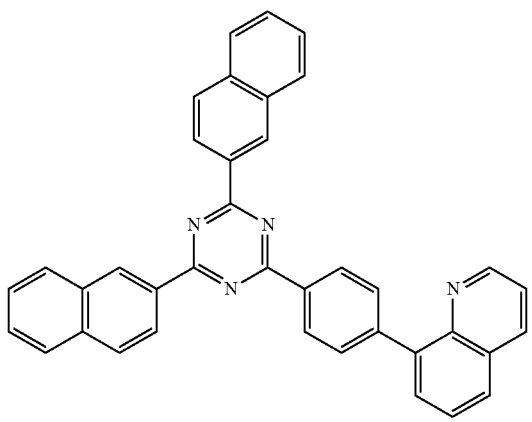

ET28
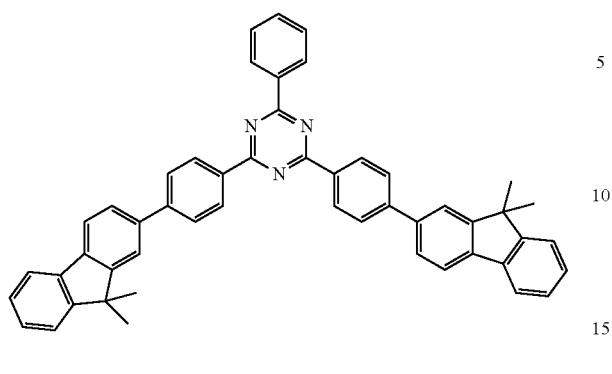
ET31
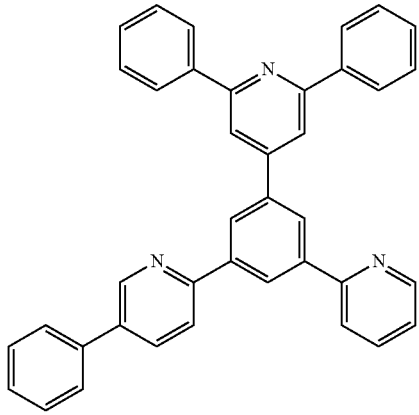
ET29
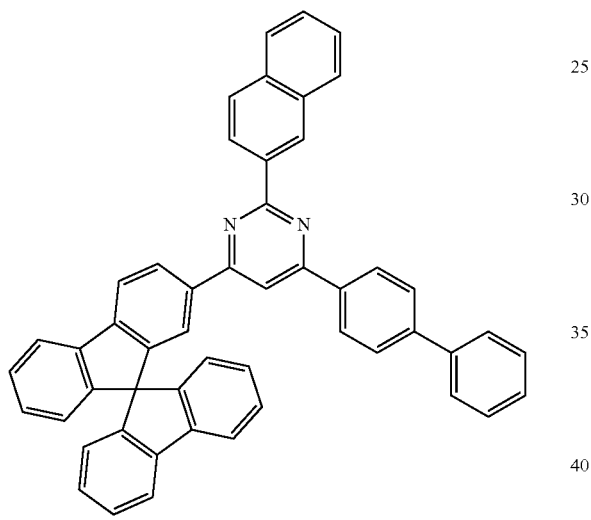
ET32
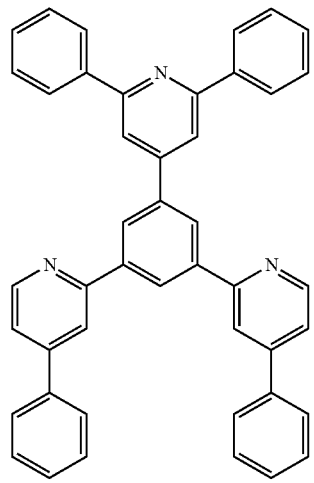
ET30
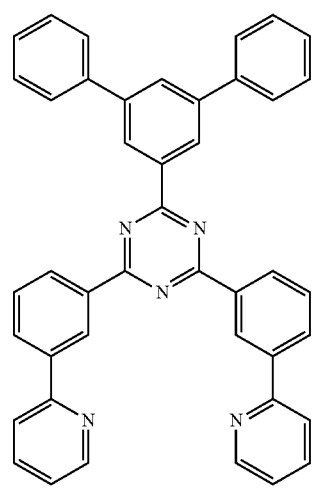
ET33
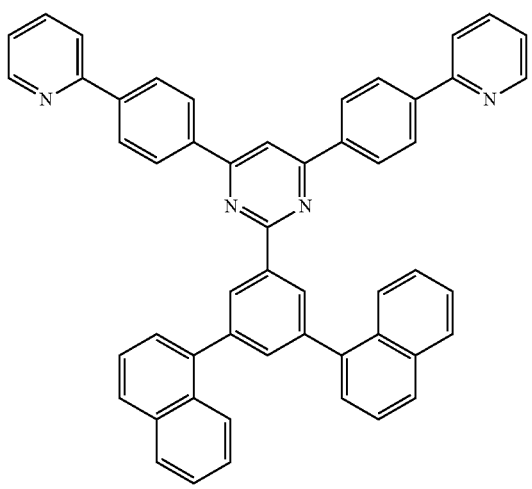

-continued

ET34

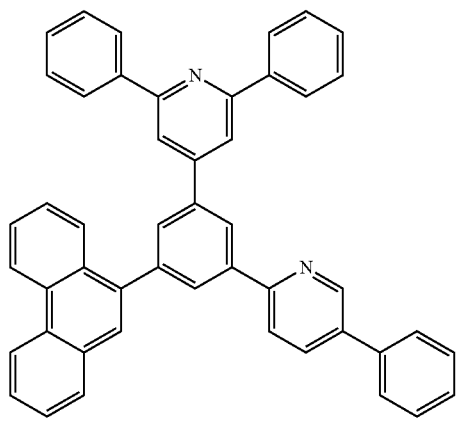

ET35

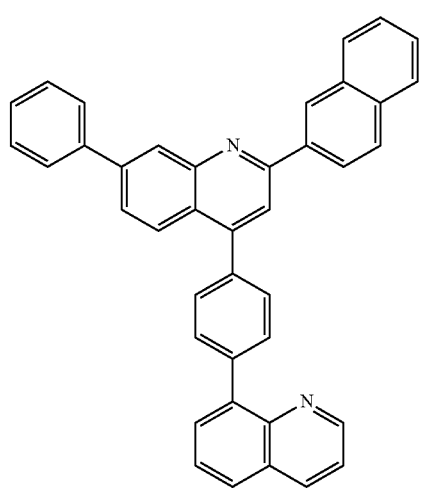

ET36

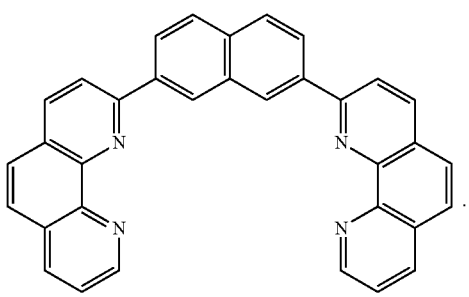

In one or more embodiments, the electron transport region may include at least one selected from 2,9-dimethyl-4,7-diphenyl-1,10-phenanthroline (BCP), 4,7-dphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

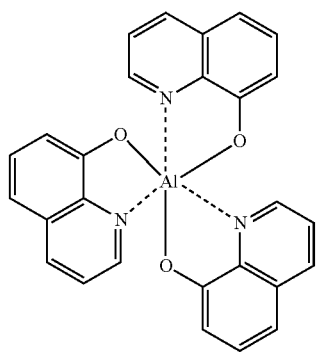

Alq₃

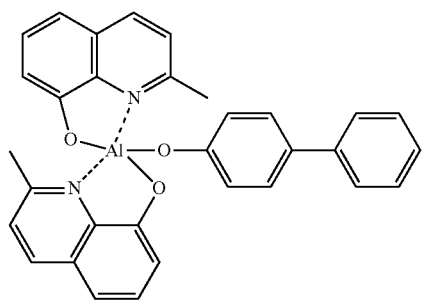

BAlq

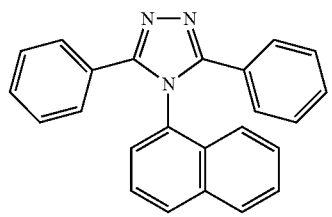

TAZ

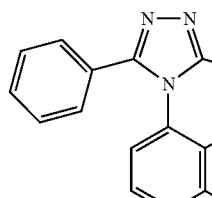

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within any of the foregoing ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within any of the foregoing ranges, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth metal complex. The alkali metal complex may include a metal ion selected from a Li ion, a Na ion, a K ion, a Rb ion, and a Cs ion, and the alkaline earth metal complex may include a metal ion selected from a Be ion, a Mg ion, a Ca ion, a Sr ion, and a Ba ion. A ligand coordinated with the metal ion of the alkali metal complex or the alkaline earth metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

ET-D1

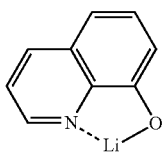

ET-D2

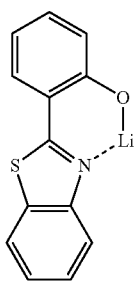

The electron transport region may include an electron injection layer that facilitates injection of electrons from the second electrode 190. The electron injection layer may directly contact the second electrode 190.

The electron injection layer may have i) a single-layered structure including a single (or sole) layer including a single (or sole) material, ii) a single-layered structure including a single (or sole) layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combinations thereof.

The alkali metal may be selected from Li, Na, K, Rb, and Cs. In one or more embodiments, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In one or more embodiments, the alkali metal compound may be selected from LiF, $Li_2O$, NaF, LiI, NaI, CsI, and KI, but embodiments of the present disclosure are not limited thereto.

The alkaline earth metal compound may be selected from alkaline earth metal oxides, such as BaO, SrO, CaO, $Ba_xSr_{1-x}O$ (0<x<1), $Ba_xCa_{1-x}O$ (0<x<1). In one or more embodiments, the alkaline earth metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one or more embodiments, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth metal complex, and the rare earth metal complex may include an ion of alkali metal, alkaline earth-metal, and rare earth metal as described above, and a ligand coordinated with a metal ion of the alkali metal complex, the alkaline earth metal complex, or the rare earth metal complex may be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within any of the foregoing ranges, the electron injection layer may have suitable or satisfactory electron injection characteristics without a substantial increase in driving voltage.

[Second Electrode 190]

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

[Description of FIGS. 5 to 7]

An organic light-emitting device 20 of FIG. 5 includes a first capping layer 210, a first electrode 110, an organic layer 150, and a second electrode 190 which are sequentially stacked in this stated order, an organic light-emitting device 30 of FIG. 6 includes a first electrode 110, an organic layer 150, a second electrode 190, and a second capping layer 220 which are sequentially stacked in this stated order, and an organic light-emitting device 40 of FIG. 7 includes a first capping layer 210, a first electrode 110, an organic layer 150, a second electrode 190, and a second capping layer 220.

Regarding FIGS. 5 to 7, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one or more embodiments, at least one selected from the first capping layer 210 and the second capping layer 220 may each independently include an amine-based compound.

In one or more embodiments, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

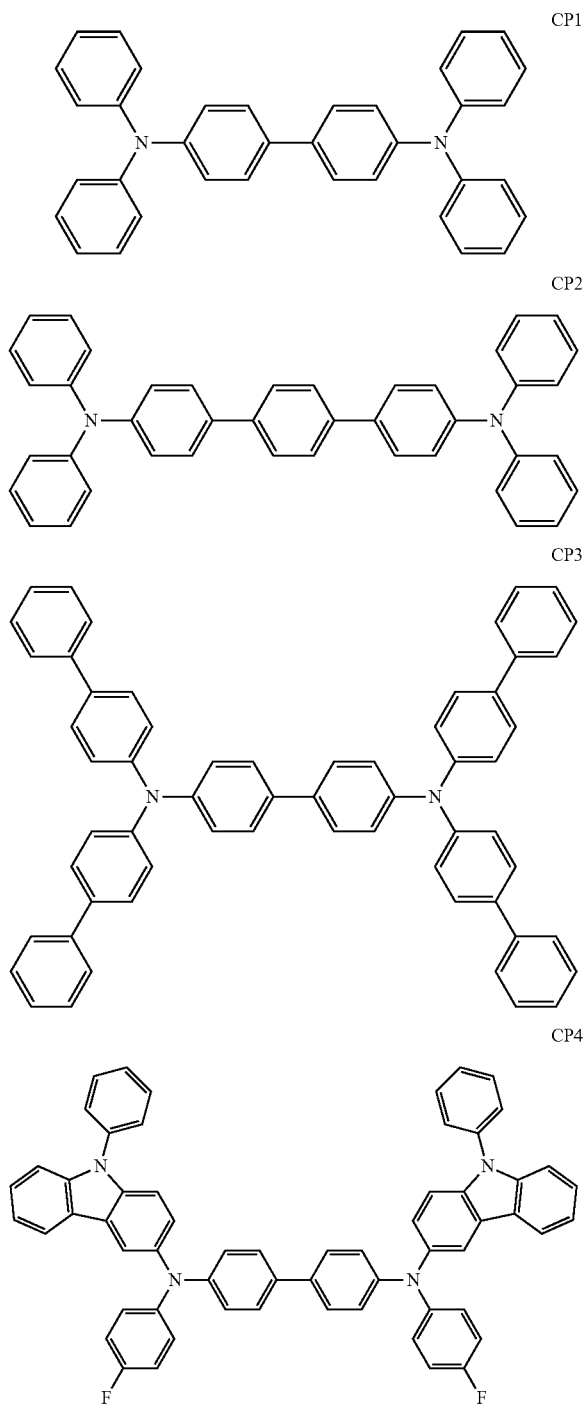

CP5

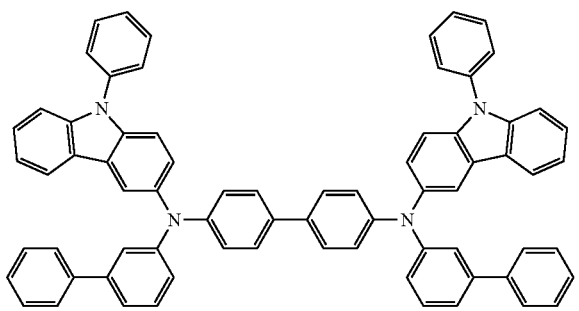

Hereinbefore, the organic light-emitting device according to an embodiment has been described in connection with FIGS. 1 and 5-7. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100° C. to about 500° C., at a vacuum degree of about $10^{-8}$ torr to about $10^{-3}$ torr, and at a deposition rate of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to about 200° C. by taking into account a material to be included in a layer to be formed, and the structure of a layer to be formed.

[General Definition of Substituents]

The term "$C_1$-$C_{60}$ alkyl group," as used herein, refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 1 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group," as used herein, indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other, only carbon atoms as ring-forming atoms, and no aromaticity in its entire molecular structure. A more detailed example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a tetravalent group.

The term "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$;

wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "But," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical or substantially identical molar equivalent of B was used in place of A.

EXAMPLE

Evaluation Example 1

Ionization energy (IP) and electron affinity (EA) of Compounds 1, 2, and 4 to 9, $F_4$-TCNQ, and Compounds A and B were calculated through simulation by using Vienna Ab-initio Simulation Package (VASP). Results thereof are shown in Table 1 below. The calculations were performed using density functional theory with the Perdew-Burke-Enzerhof (PBE) functional and the plane augmented wave (PAW) basis set. Further, the ionization energy (IP) and electron affinity were calculated according to the following equations:

$$IP = E_{cat} - E_{neutral}$$

$$EA = E_{neutral} - E_{anion}$$

Also, for reference, ionization energy and electron affinity of Compound HT3 are also shown.

TABLE 1

| Compound No. | Electron affinity (eV) | Ionization energy (eV) |
|---|---|---|
| Compound 1 | 5.565 | 9.481 |
| Compound 2 | 5.552 | 9.486 |
| Compound 4 | 5.640 | 8.588 |
| Compound 5 | 5.590 | 9.521 |
| Compound 6 | 5.358 | 8.927 |
| Compound 7 | 5.594 | 9.705 |
| Compound 8 | 5.500 | 9.789 |
| Compound 9 | 5.272 | 9.667 |
| $F_4$-TCNQ | 4.010 | 9.340 |
| Compound A | 4.190 | 8.760 |
| Compound B | 3.110 | 7.850 |
| HT3 | 0.940 | 5.710 |

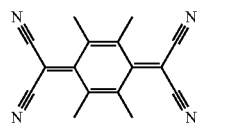

$F_4$-TCNQ

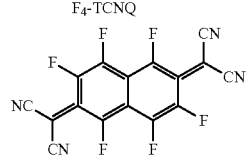

Compound A

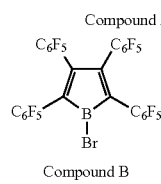

Compound B

Referring to Table 1, it can be seen that Compounds 1, 2, and 4 to 9 have a high electron affinity, as compared with $F_4$-TCNQ and Compounds A and B.

Evaluation Example 2

Hole injection barriers (HIBs) at interfaces between an anode (indium tin oxide (ITO)) and hole injection layers (HIL) (matrix:HT3, p-dopant: Compounds 1, 2, and 4 to 9, $F_4$-TCNQ, and Compounds A and B) were calculated by using Electronegativity Equalization model (EEM) based anode/p-dopant doped HTL (PHIL) interface barrier simulation technology, based on Equation (1) (Equation (1) is an equation derived from an electronegative equalization principle that neighboring atoms or molecules have substantially the same electron affinity ($\chi$)). Results thereof are shown in Table 2 below:

$$HIB = \eta^{Org} + \frac{(\chi^{Org} - \chi^M)}{(1 + \eta^M/\eta^{Org})}. \qquad \text{Equation (1)}$$

In Equation (1), $\chi$ represents electronegativity, $\eta$ represents chemical hardness, and superscripts M and Org represent a metal (for example, an anode material) and an organic material (for example, an HIL material), respectively. and $\chi$ and $\eta$ may be calculated from the ionization energy (IP) and the electron affinity (EA) by using Equation (2) below:

$$\chi = \frac{IP + EA}{2}, \eta = \frac{IP - EA}{2} \qquad \text{Equation (2)}$$

Based on Equation (2), $\chi^M$ is 5.85 eV, and $\eta^M$ is 1.7 eV.

TABLE 2

| Compound No. | Hole injection barrier (eV) |
|---|---|
| Compound 1 | 0.13 |
| Compound 2 | 0.13 |
| Compound 4 | 0.1 |
| Compound 5 | 0.15 |
| Compound 6 | 0.24 |
| Compound 7 | 0.12 |
| Compound 8 | 0.21 |
| Compound 9 | 0.12 |
| $F_4$-TCNQ | 0.55 |
| Compound A | 0.58 |
| Compound B | 0.68 |
| HT3 | 0.9 |

Evaluation Example 3

$\chi$ and $\eta$ of the PHIL (a case where a molar ratio of the p-dopant is taken into account) may be calculated from EA and IP values of the HIL material and the p-dopant. An equation for calculating $\chi$ and $\eta$ of the PHIL is as follows:

$$N^H \exp\left[-\frac{\chi^{PHIL} - IP^H}{kT}\right] = \qquad \text{Equation (3)}$$

$$(N^H - N^D)\exp\left[-\frac{EA^H - IP^H}{2\,kT}\right] + N^D \exp\left[-\frac{EA^D - IP^H}{2\,kT}\right]$$

-continued $$\chi^{PHIL} = IP^H - kT\log\left\{\exp\left[-\frac{EA^H - IP^H}{2\,kT}\right] - \frac{N^D}{N^H}\left(\exp\left[-\frac{EA^H - IP^H}{2\,kT}\right] - \exp\left[-\frac{EA^D - IP^H}{2\,kT}\right]\right)\right\}$$ Equation (4)

$$\eta^{PHIL} = IP^H - \chi^{PHIL}.$$ Equation (5)

In Equations (3) to (5), N, k, and T represent a molar ratio, a Boltzmann constant, and temperature (room temperature), respectively, a superscript H represents the HIL material, and D represents the p-dopant.

In Equations (3) and (4), $EA^H = 0.94$ eV, and $IP^H = 5.71$ eV.

If $\chi^{PHIL}$ and $\eta^{PHIL}$ calculated from Equations (4) and (5) are substituted into $\chi^{Org}$ and $\eta^{Org}$ in Equation (1), anode/PHIL HIB based on the molar ratio of the p-dopant may be calculated. Results thereof are shown in FIG. 4 below.

Figure 4:
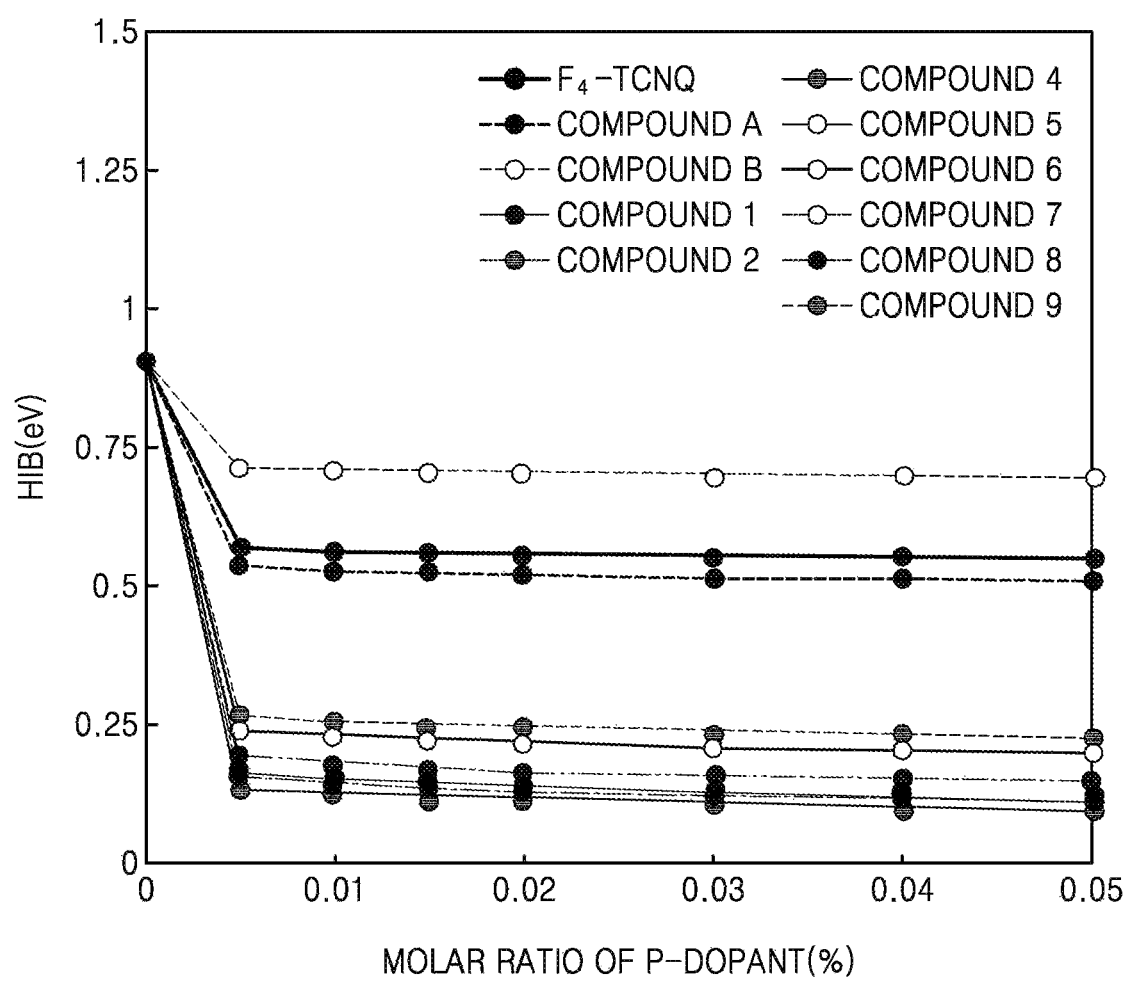
FIG. 4 is a graph showing a function of a hole injection barrier (HIB) according to Evaluation Example 3.

Referring to FIG. 4, it can be seen that an organic light-emitting device including Compounds 1, 2, and 4 to 9 has a low hole injection barrier (HIB), as compared with an organic light-emitting device including $F_4$-TCNQ, and Compounds A and B.

According to one or more embodiments, an organic light-emitting device including the borole compound may have high efficiency and a low driving voltage.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure. In the drawings, the relative sizes of elements, layers, and regions may be exaggerated for clarity.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on" another element or layer, it can be directly on the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A borole compound represented by Formula 1:

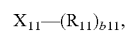

Formula 1 wherein, in Formula 1,
$X_{11}$ is selected from a substituted or unsubstituted triazine, a substituted or unsubstituted vinylene carbonate, a substituted or unsubstituted thiophene, a substituted or unsubstituted furan, a substituted or unsubstituted dibenzoborole, a substituted or unsubstituted azulene, a substituted or unsubstituted naphthalene, a substituted or unsubstituted anthracene, and a substituted or unsubstituted pyrene, and $R_{11}$ is represented by one of Formulae 2-1 to 2-3:

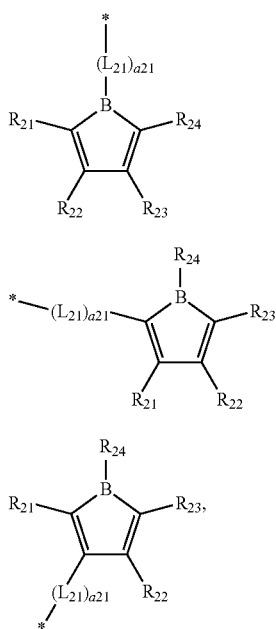

wherein b11 is selected from 1, 2, 3, 4, 5, 6, 7, 8, 9, and 10, wherein, when b11 is two or more, a plurality of $R_{11}$(s) are identical to or different from each other, in Formulae 2-1 to 2-3, $L_{21}$ is selected from a substituted or unsubstituted $C_1$-$C_{10}$ alkylene group, a substituted or unsubstituted $C_2$-$C_{10}$ alkenylene group, a $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a21 is 0 or 1, $R_{21}$ to $R_{24}$ are each independently selected from $R_{EW}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), provided that at least one of $R_{21}$ to $R_{24}$ is $R_{EW}$, $R_{EW}$ is an electron withdrawing group, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to a neighboring atom.

2. The borole compound of claim 1, wherein:

$X_{11}$ is represented by one of Formulae 3-1 to 3-9:

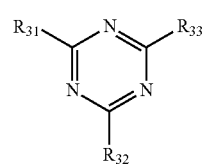

3-1

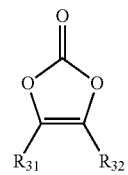

3-2

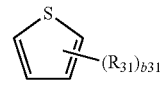

3-3

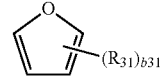

3-4

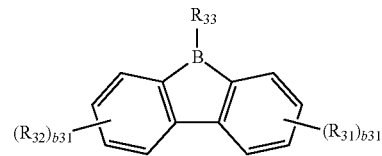

3-5

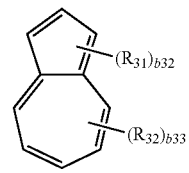

3-6

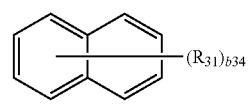

3-7

-continued

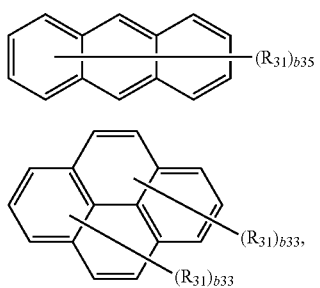
3-8

3-9 wherein, in Formulae 3-1 to 3-9, $R_{31}$ to $R_{33}$ are each independently selected from:

a binding site to $R_{11}$, hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group, at least one selected from $R_{31}$, the number of which is the same as b11, is a binding site to $R_{11}$, at least one selected from $R_{31}$ and $R_{32}$, the number of which is the same as b11, is a binding site to $R_{11}$, or at least one selected from $R_{31}$ to $R_{33}$, the number of which is the same as b11, is a binding site to $R_{11}$, b31 is selected from 1, 2, 3, and 4, b32 is selected from 1, 2, and 3, b33 is selected from 1, 2, 3, 4, and 5, b34 is selected from 1, 2, 3, 4, 5, and 6, and b35 is selected from 1, 2, 3, 4, 5, 6, 7, 8, 9, and 10.

3. The borole compound of claim 1, wherein:

$X_{11}$ is represented by one of Formulae 4-1 to 4-9:

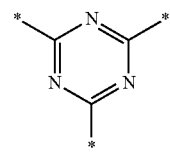
4-1

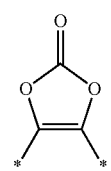
4-2

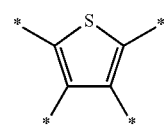
4-3

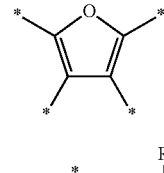
4-4

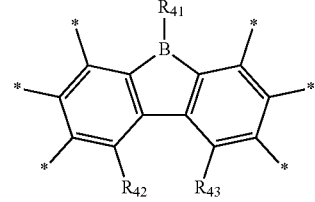
4-5

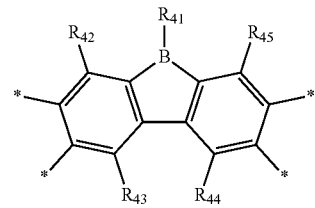
4-6

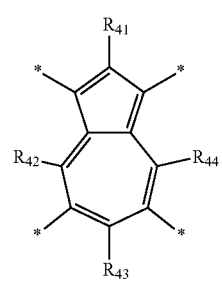
4-7

-continued 4-8

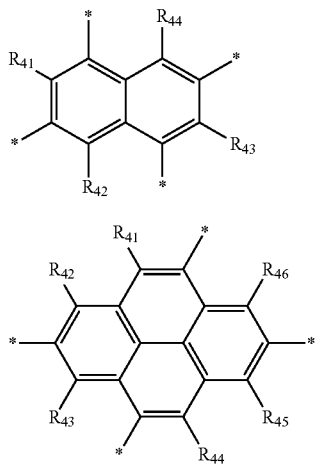

4-9 wherein, in Formula 4-1 to 4-9,

* indicates a binding site to $R_{11}$, and $R_{41}$ to $R_{46}$ are each independently selected from:

hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

4. The borole compound of claim 1, wherein:

$R_{11}$ is represented by Formula 2-1.

5. The borole compound of claim 1, wherein:

$L_{21}$ is selected from:

a phenylene group, a naphthylene group, a pyridinylene group, a pyrimidinylene group, a pyrazinylene group, and a triazinylene group; and a phenylene group, a naphthylene group, a pyridinylene group, a pyrimidinylene group, a pyrazinylene group, and a triazinylene group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group.

6. The borole compound of claim 1, wherein:

a21 is 0.

7. The borole compound of claim 1, wherein:

$R_{21}$ to $R_{24}$ are each independently selected from:

$R_{EW}$, hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, and a $C_1$-$C_{10}$ alkoxy group;

a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{10}$ arylthio group, a $C_1$-$C_{10}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{10}$ aryloxy group, a $C_6$-$C_{60}$ arylthio group, a $C_1$-$C_{10}$ heteroaryl group, a monovalent non-aromatic condensed polycyclic group, and a monovalent non-aromatic condensed heteropolycyclic group, provided that at least one of $R_{21}$ to $R_{24}$ is $R_{EW}$.

8. The borole compound of claim 1, wherein:

$R_{21}$ to $R_{24}$ are each independently selected from:

$R_{EW}$, hydrogen, deuterium, —F, —Cl, —Br, —I, a hydroxyl group, a cyano group, a nitro group, a $C_1$-$C_{10}$ alkyl group, and a $C_1$-$C_{10}$ alkoxy group;

a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group; and a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_2$-$C_{10}$ alkenyl group, a phenyl group, a naphthyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, and an isoquinolinyl group, provided that at least one of $R_{21}$ to $R_{24}$ is $R_{EW}$.

9. The borole compound of claim 1, wherein:

$R_{21}$ to $R_{24}$ are each independently selected from:

$R_{EW}$, hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group, provided that at least one of $R_{21}$ to $R_{24}$ is $R_{EW}$.

10. The borole compound of claim 1, wherein:

$R_{11}$ is represented by one of Formulae 2-11 to 2-19:

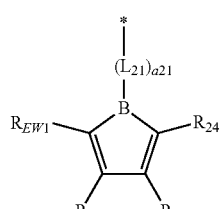
2-11

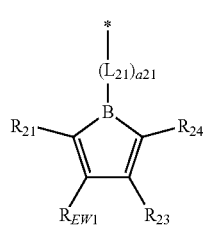
2-12

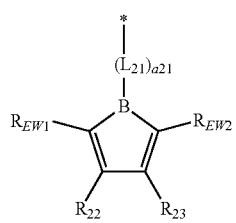
2-13

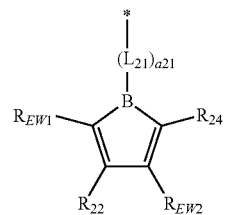
2-14

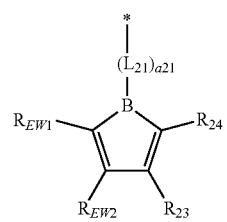
2-15

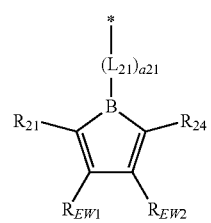
2-16

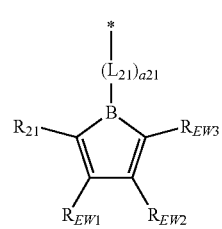
2-17

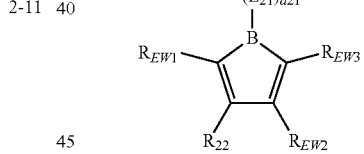
2-18

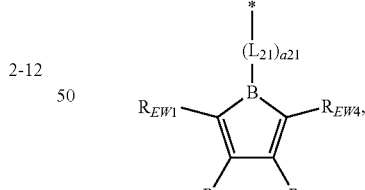
2-19 wherein, in Formulae 2-11 to 2-19, $L_{21}$ is selected from a phenylene group, a naphthylene group, a pyridinylene group, a pyrimidinylene group, a pyrazinylene group, and a triazinylene group, a21 is 0 or 1, $R_{21}$ to $R_{24}$ are each independently selected from:

$R_{EW}$, hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;
a phenyl group and a naphthyl group; and
a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group,
$R_{EW1}$ to $R_{EW4}$ are each an electron withdrawing group, and
* indicates a binding site to a neighboring atom.

11. The borole compound of claim 1, wherein:
$R_{11}$ is represented by Formula 2-19:

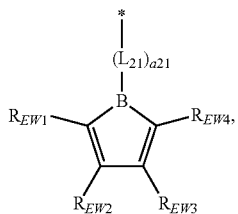

2-19 wherein, in Formula 2-19,
$(L_{21})_{a21}$ is a single bond,
$R_{EW1}$ to $R_{EW4}$ are each independently selected from —F, —Cl, —Br, —I, a cyano group, a nitro group, —CF$_3$, —CCl$_3$, —CBr$_3$, —CI$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, and
* indicates a binding site to $X_{11}$.

12. The borole compound of claim 1, wherein:
$R_{EW}$ is selected from:
—F, —Cl, —Br, —I, a cyano group, and a nitro group; and
a C$_1$-C$_{10}$ alkyl group and a C$_2$-C$_{10}$ alkenyl group, each substituted with at least one selected from —F, —Cl, —Br, —I, a cyano group, and a nitro group.

13. The borole compound of claim 1, wherein:
$X_{11}$ is represented by one of Formulae 4-1 to 4-9,
$R_{11}$ is represented by Formula 2-19, and
b11 is selected from 1, 2, 3, 4, 5, 6, 7, 8, 9, and 10, wherein, when b11 is two or more, a plurality of $R_{11}$(s) are identical to or different from each other:

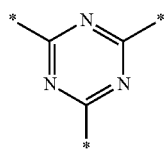

4-1

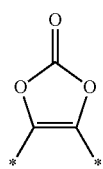

4-2

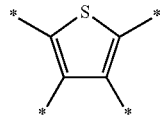

4-3

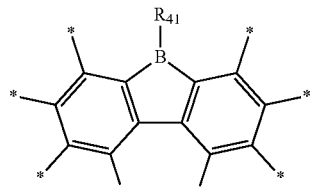

4-4

4-5

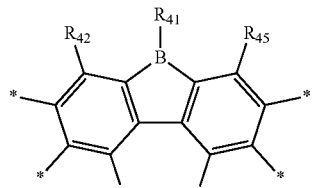

4-6

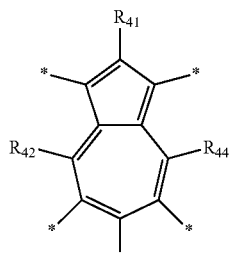

4-7

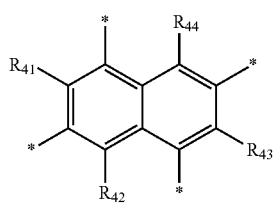

4-8

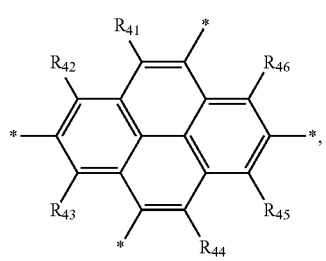

4-9 wherein, in Formulae 4-1 to 4-9,
* indicates a binding site to $R_{11}$,
$R_{41}$ to $R_{46}$ are each independently selected from:
hydrogen, deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, and a tert-butoxy group;

a phenyl group and a naphthyl group; and a phenyl group and a naphthyl group, each substituted with at least one selected from deuterium, —F, —Cl, —Br, —I, a hydroxyl group, a cyano group, a nitro group, a methyl group, an ethyl group, an n-propyl group, an iso-propyl group, an n-butyl group, a sec-butyl group, an iso-butyl group, a tert-butyl group, a methoxy group, an ethoxy group, an n-propoxy group, an iso-propoxy group, an n-butoxy group, a sec-butoxy group, an iso-butoxy group, a tert-butoxy group, a phenyl group, and a naphthyl group,

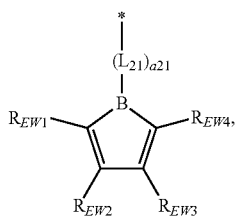

2-19 wherein, in Formula 2-19, $(L_{21})_{a21}$ is a single bond, $R_{EW1}$ to $R_{EW4}$ are each independently selected from —F, —Cl, —Br, —I, a cyano group, a nitro group, —CF$_3$, —CCl$_3$, —CBr$_3$, —CI$_3$, —C$_2$F$_3$, —C$_2$Cl$_3$, —C$_2$Br$_3$, —C$_2$I$_3$, —C$_2$(CN)$_3$, and —C$_2$(NO$_2$)$_3$, and

* indicates a binding site to $X_{11}$.

14. The borole compound of claim 1, wherein:
the borole compound is selected from Compounds 1 to 9:

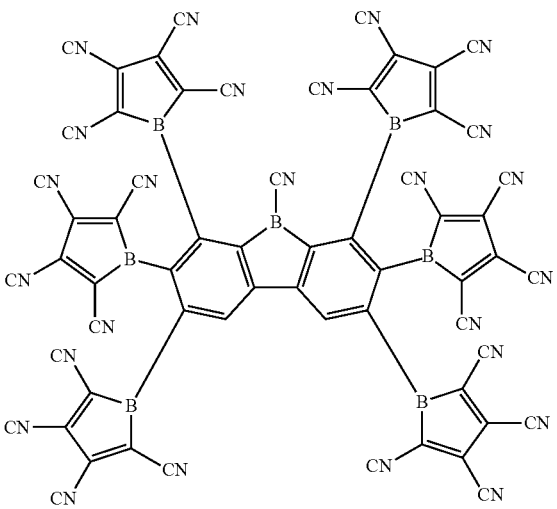

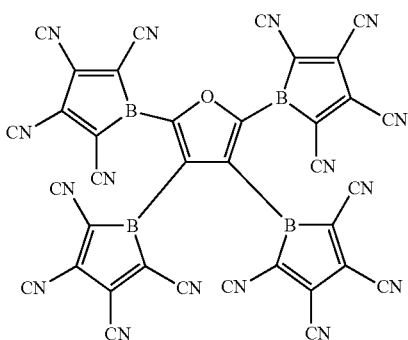

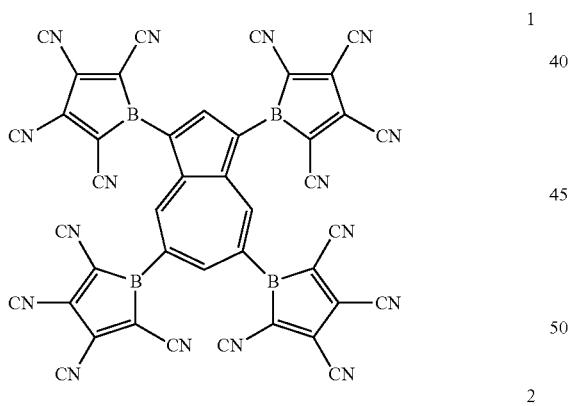

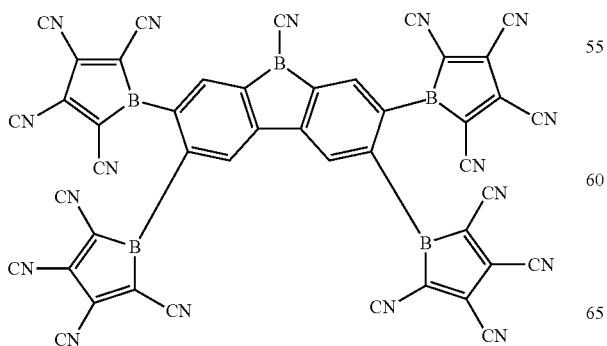

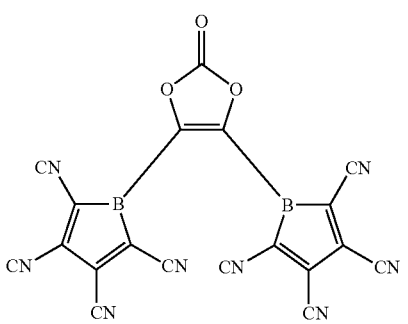

-continued

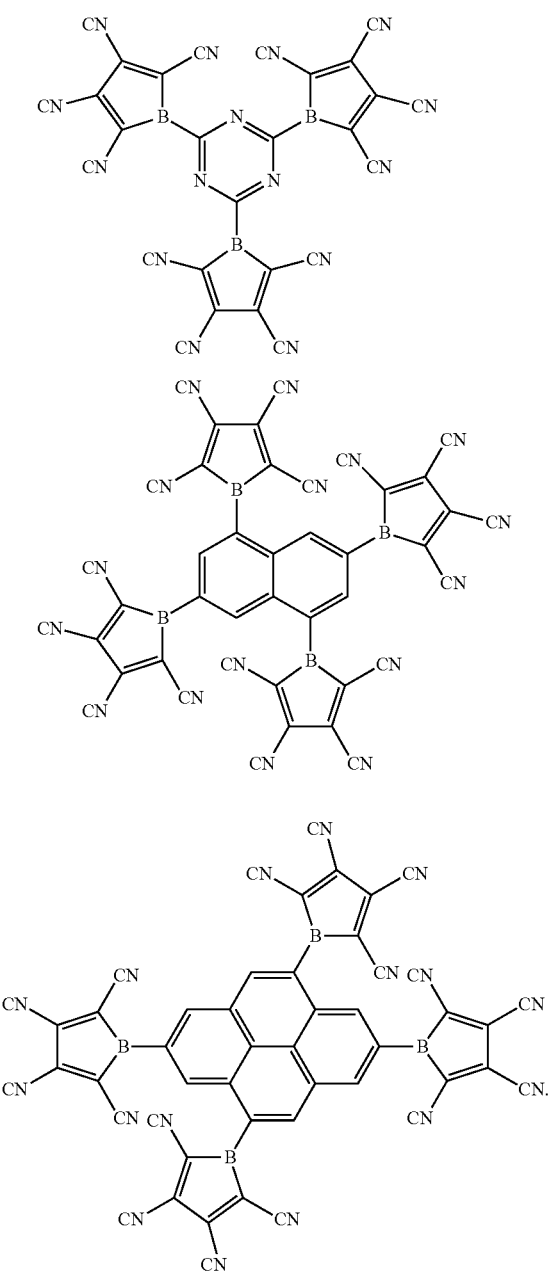

15. The borole compound of claim 1, wherein:
an electron affinity of the borole compound is in a range of about 5.5 eV to about 6.0 eV.

16. The borole compound of claim 1, wherein:
a hole injection barrier of the borole compound is in a range of about 0.1 eV to about 0.4 eV.

17. An organic light-emitting device comprising:
a first electrode;
a second electrode; and
an organic layer between the first electrode and the second electrode, the organic layer comprising an emission layer,
wherein the organic layer comprises the borole compound of claim 1.

18. The organic light-emitting device of claim 17, wherein:
the first electrode is an anode,
the second electrode is a cathode,
the organic layer further comprises a hole transport region between the first electrode and the emission layer, and
the hole transport region comprises the borole compound.

19. The organic light-emitting device of claim 18, wherein:
the hole transport region comprises a hole injection layer comprising the borole compound, or
the hole transport region comprises a buffer layer comprising the borole compound.

20. The organic light-emitting device of claim 19, wherein:
the hole injection layer comprising the borole compound further comprises a matrix material, and an amount of the borole compound in the hole injection layer is in a range of greater than 0 wt % and equal to or smaller than 6 wt % based on a total weight of the hole injection layer; or
the buffer layer comprising the borole compound further comprises a matrix material, and an amount of the borole compound in the buffer layer is in a range of greater than 0 wt % and equal to or smaller than 6 wt % based on the total weight of the buffer layer.

* * * * *